US007618151B2

(12) United States Patent
Abbondanzio et al.

(10) Patent No.: US 7,618,151 B2
(45) Date of Patent: Nov. 17, 2009

(54) COMBINATION COMPACT FLOURESCENT LIGHT WITH ACTIVE INGREDIENT EMISSION

(75) Inventors: Matthew Abbondanzio, Racine, WI (US); Simon M. Conway, Burlington, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 12/057,049

(22) Filed: Mar. 27, 2008

(65) Prior Publication Data

US 2008/0232091 A1    Sep. 25, 2008

Related U.S. Application Data

(63) Continuation-in-part of application No. 11/553,127, filed on Oct. 26, 2006, now Pat. No. 7,484,860, which is a continuation-in-part of application No. 11/426,055, filed on Jun. 23, 2006, now Pat. No. 7,318,659, which is a continuation-in-part of application No. 11/069,964, filed on Mar. 3, 2005, now Pat. No. 7,246,919, application No. 12/057,049, which is a continuation-in-part of application No. 10/561,822, filed on Apr. 25, 2006.

(60) Provisional application No. 60/549,154, filed on Mar. 3, 2004, provisional application No. 60/483,913, filed on Jul. 2, 2003.

(51) Int. Cl.
*F21V 33/00* (2006.01)
(52) U.S. Cl. ............................ 362/96; 362/643; 362/253
(58) Field of Classification Search .................. 362/96, 362/253, 643, 650, 651, 652
See application file for complete search history.

(56) References Cited

U.S. PATENT DOCUMENTS

| 1,535,486 A | 4/1925 | Lundy |
| 1,565,500 A | 12/1925 | Ritter |
| 1,706,939 A | 3/1929 | Rosenthal |
| 1,732,707 A | 10/1929 | Winsboro |
| 1,920,599 A | 8/1933 | Schuh |

(Continued)

FOREIGN PATENT DOCUMENTS

WO    WO 01/78488 A2    10/2001

(Continued)

OTHER PUBLICATIONS

PCT/US2007/022730, Written Opinion of the ISA.

(Continued)

*Primary Examiner*—Sandra L O'Shea
*Assistant Examiner*—Evan Dzierzynski

(57) ABSTRACT

A substitute for a conventional incandescent light bulb includes a CFL with a specially equipped base structure disposed between the male connector and the coiled fluorescent tube. The modified base includes an active vapor dispenser and, preferably, a heater for increasing and/or controlling the rate of active vapor emission. The male connector may be a threaded male Edison-type connector or any other type of male connector for use with female light sockets. The disclosed devices provide an energy-efficient source of white light and controlled active or fragrance emission. The base may also be equipped with one or more electrical connection ports for connection the base to one or more accessories such as volatile active dispensers or colored light emitting devices.

17 Claims, 11 Drawing Sheets

U.S. PATENT DOCUMENTS

| | | | |
|---|---|---|---|
| 2,124,543 A | 7/1938 | Clyne | |
| 2,143,246 A | 1/1939 | McGary | |
| 2,372,371 A | 3/1945 | Eisner | |
| 2,435,756 A | 2/1948 | Schlesinger | |
| 2,468,164 A | 4/1949 | Brewster | |
| 2,469,656 A | 5/1949 | Lienert | |
| 2,535,802 A | 12/1950 | Libson | |
| 2,694,771 A | 11/1954 | Cox | |
| 2,741,812 A | 4/1956 | Tellier | |
| 2,741,813 A | 4/1956 | Rubin | |
| 2,757,278 A | 7/1956 | Cloud | |
| 2,799,166 A | 7/1957 | Leftwich | |
| 2,818,770 A | 1/1958 | Cilurzo | |
| 2,931,880 A | 4/1960 | Yaffe | |
| 3,080,624 A | 3/1963 | Weber, III | |
| 3,119,565 A | 1/1964 | Nottingham | |
| 3,377,126 A | 4/1968 | Nijland et al. | |
| 3,760,179 A | 9/1973 | Addington, Jr. | |
| 3,763,347 A | 10/1973 | Whitaker | |
| 3,893,019 A * | 7/1975 | King et al. | 323/327 |
| 3,923,458 A | 12/1975 | Moran | |
| 3,948,445 A | 4/1976 | Andeweg | |
| 4,009,384 A | 2/1977 | Holland | |
| 4,045,664 A | 8/1977 | Vrenken et al. | |
| 4,184,099 A | 1/1980 | Lindauer et al. | |
| 4,234,907 A | 11/1980 | Daniel | |
| 4,346,059 A | 8/1982 | Spector | |
| 4,391,781 A | 7/1983 | van Lit | |
| 4,463,286 A | 7/1984 | Justice | |
| 4,493,011 A | 1/1985 | Spector | |
| 4,510,555 A | 4/1985 | Mori | |
| 4,519,017 A | 5/1985 | Daniel | |
| 4,544,592 A | 10/1985 | Spector | |
| 4,549,250 A | 10/1985 | Spector | |
| 4,561,043 A | 12/1985 | Thompson | |
| 4,579,717 A | 4/1986 | Gyulay | |
| 4,640,266 A | 2/1987 | Levy | |
| 4,647,428 A | 3/1987 | Gyulay | |
| 4,647,433 A | 3/1987 | Spector | |
| 4,714,984 A | 12/1987 | Spector | |
| 4,754,372 A | 6/1988 | Harrison | |
| 4,849,181 A | 7/1989 | Kelley et al. | |
| 4,849,606 A | 7/1989 | Martens, III et al. | |
| 4,875,144 A | 10/1989 | Wainwright | |
| 4,885,663 A | 12/1989 | Parker | |
| 4,933,815 A | 6/1990 | Parthasarathy | |
| 4,955,975 A | 9/1990 | Mori | |
| 4,965,490 A | 10/1990 | Ratner | |
| 4,965,701 A | 10/1990 | Voland | |
| 4,972,305 A | 11/1990 | Blackburn | |
| 4,974,136 A | 11/1990 | Noori-Shad et al. | |
| 5,021,928 A | 6/1991 | Daniel | |
| 5,046,837 A | 9/1991 | Stroomer et al. | |
| 5,066,085 A | 11/1991 | Gimbutas et al. | |
| 5,069,877 A | 12/1991 | Pozzo | |
| 5,178,839 A | 1/1993 | Spector | |
| 5,183,323 A | 2/1993 | Daniel | |
| 5,217,696 A | 6/1993 | Wolverton et al. | |
| 5,247,491 A | 9/1993 | Kwiatkowski | |
| 5,249,105 A | 9/1993 | Koizumi | |
| 5,251,116 A | 10/1993 | Wijbenga et al. | |
| 5,301,090 A | 4/1994 | Hed | |
| 5,402,517 A | 3/1995 | Gillett et al. | |
| 5,426,474 A | 6/1995 | Rubtsov et al. | |
| 5,432,876 A | 7/1995 | Appeldorn et al. | |
| D363,537 S | 10/1995 | Moody | |
| 5,455,750 A | 10/1995 | Davis et al. | |
| 5,546,291 A * | 8/1996 | Simes | 362/223 |
| 5,547,616 A | 8/1996 | Dancs et al. | |
| 5,556,191 A | 9/1996 | Maassen | |
| 5,561,346 A | 10/1996 | Byrne | |
| 5,568,964 A | 10/1996 | Parker et al. | |
| 5,647,052 A | 7/1997 | Patel et al. | |
| 5,651,942 A | 7/1997 | Christensen | |
| 5,688,042 A | 11/1997 | Madadi et al. | |
| 5,691,886 A | 11/1997 | Stacy | |
| 5,703,440 A | 12/1997 | Kachmarik et al. | |
| 5,711,591 A | 1/1998 | Jordan | |
| 5,801,484 A | 9/1998 | Bankuti et al. | |
| 5,823,652 A | 10/1998 | Vann | |
| 5,908,231 A | 6/1999 | Huff | |
| 6,016,038 A | 1/2000 | Mueller et al. | |
| 6,064,155 A * | 5/2000 | Maya et al. | 315/56 |
| 6,099,137 A | 8/2000 | McCormack et al. | |
| 6,106,786 A | 8/2000 | Akahoshi | |
| 6,120,737 A | 9/2000 | Zembrodt | |
| 6,143,313 A | 11/2000 | Ito et al. | |
| 6,150,774 A | 11/2000 | Mueller et al. | |
| 6,166,496 A | 12/2000 | Lys et al. | |
| 6,200,002 B1 | 3/2001 | Marshall et al. | |
| 6,211,626 B1 | 4/2001 | Lys et al. | |
| 6,217,188 B1 | 4/2001 | Wainwright et al. | |
| 6,220,722 B1 | 4/2001 | Begemann | |
| 6,220,742 B1 | 4/2001 | Lloyd et al. | |
| 6,234,645 B1 | 5/2001 | Borner et al. | |
| 6,234,648 B1 | 5/2001 | Borner et al. | |
| 6,234,649 B1 | 5/2001 | Katougi | |
| 6,254,248 B1 | 7/2001 | McAuley et al. | |
| 6,270,720 B1 | 8/2001 | Mandish | |
| 6,292,901 B1 | 9/2001 | Lys et al. | |
| 6,294,800 B1 | 9/2001 | Duggal et al. | |
| 6,299,338 B1 | 10/2001 | Levinson et al. | |
| 6,302,559 B1 * | 10/2001 | Warren | 362/643 |
| 6,318,876 B1 | 11/2001 | Sigro et al. | |
| 6,339,298 B1 | 1/2002 | Chen | |
| 6,340,868 B1 | 1/2002 | Lys et al. | |
| 6,371,450 B1 | 4/2002 | Davis et al. | |
| 6,371,634 B1 | 4/2002 | Tufte | |
| D457,667 S | 5/2002 | Piepgras et al. | |
| D457,669 S | 5/2002 | Piepgras et al. | |
| D457,974 S | 5/2002 | Piepgras et al. | |
| 6,391,329 B1 | 5/2002 | Ito et al. | |
| D458,395 S | 6/2002 | Piepgras et al. | |
| 6,400,104 B1 | 6/2002 | Ham | |
| 6,402,347 B1 | 6/2002 | Maas et al. | |
| 6,406,172 B1 | 6/2002 | Harbers et al. | |
| 6,416,180 B1 | 7/2002 | Strobl | |
| D463,610 S | 9/2002 | Piepgras et al. | |
| 6,459,919 B1 | 10/2002 | Lys et al. | |
| 6,472,876 B1 | 10/2002 | Notohamiprodjo et al. | |
| 6,478,440 B1 * | 11/2002 | Jaworski et al. | 362/96 |
| 6,478,453 B2 | 11/2002 | Lammers et al. | |
| 6,480,649 B2 | 11/2002 | Lee | |
| D468,035 S | 12/2002 | Blanc et al. | |
| 6,488,393 B1 | 12/2002 | Burnham | |
| 6,499,860 B2 | 12/2002 | Begemann | |
| 6,513,954 B2 | 2/2003 | Ebersole | |
| 6,528,954 B1 | 3/2003 | Lys et al. | |
| 6,536,910 B2 | 3/2003 | Lin | |
| 6,536,914 B2 | 3/2003 | Hoelen et al. | |
| 6,539,656 B2 | 4/2003 | Maas et al. | |
| 6,543,925 B2 | 4/2003 | Kuykendal et al. | |
| 6,547,416 B2 | 4/2003 | Pashley et al. | |
| 6,547,423 B2 | 4/2003 | Marshall et al. | |
| 6,548,967 B1 | 4/2003 | Dowling et al. | |
| 6,558,022 B2 | 5/2003 | Kawahara | |
| 6,573,536 B1 | 6/2003 | Dry | |
| 6,577,080 B2 | 6/2003 | Lys et al. | |
| 6,586,882 B1 | 7/2003 | Harbers | |
| 6,601,982 B1 | 8/2003 | Begemann et al. | |
| 6,608,453 B2 | 8/2003 | Morgan et al. | |
| 6,613,288 B2 | 9/2003 | Gupte | |
| 6,624,597 B2 | 9/2003 | Dowling et al. | |
| 6,626,554 B2 | 9/2003 | Rincover et al. | |

| | | | | | | |
|---|---|---|---|---|---|---|
| 6,627,857 B1 | 9/2003 | Tanner et al. | | 7,109,665 B2 | 9/2006 | Green |
| 6,628,885 B1 | 9/2003 | Wilkie et al. | | 7,116,294 B2 | 10/2006 | Stopa |
| 6,629,772 B2 | 10/2003 | Brunfeld | | 7,160,012 B2 | 1/2007 | Hilscher et al. |
| 6,642,669 B1 | 11/2003 | MacAdam et al. | | 7,175,302 B2 | 2/2007 | Kazar et al. |
| 6,648,486 B2 | 11/2003 | Harbers et al. | | 2001/0014019 A1 | 8/2001 | Begemann |
| 6,648,496 B1 | 11/2003 | Elghoroury et al. | | 2001/0035853 A1 | 11/2001 | Hoelen et al. |
| 6,655,824 B2 | 12/2003 | Tufte | | 2001/0038532 A1 | 11/2001 | Harbers et al. |
| 6,672,734 B2 | 1/2004 | Lammers | | 2001/0049893 A1 | 12/2001 | Maas et al. |
| 6,676,282 B2 | 1/2004 | Begemann et al. | | 2002/0006044 A1 | 1/2002 | Harbers et al. |
| 6,688,753 B2 | 2/2004 | Calon et al. | | 2002/0030997 A1 | 3/2002 | Tufte |
| 6,712,494 B1 | 3/2004 | Hodge | | 2002/0071285 A1 | 6/2002 | Tufte |
| 6,717,376 B2 | 4/2004 | Lys et al. | | 2002/0075671 A1 | 6/2002 | Tufte |
| 6,720,745 B2 | 4/2004 | Lys et al. | | 2002/0075674 A1 | 6/2002 | Tufte |
| 6,726,341 B2 | 4/2004 | Pashley et al. | | 2002/0105800 A1 | 8/2002 | Tufte |
| 6,733,161 B2 | 5/2004 | Tufte | | 2002/0118538 A1 | 8/2002 | Calon et al. |
| D491,678 S | 6/2004 | Piepgras et al. | | 2002/0131273 A1 | 9/2002 | Tufte |
| D492,042 S | 6/2004 | Piepgras et al. | | 2002/0135997 A1 | 9/2002 | Lammers |
| 6,742,914 B2 | 6/2004 | Prodell | | 2002/0136017 A1 | 9/2002 | Tufte |
| 6,745,506 B2 | 6/2004 | Maas et al. | | 2002/0141058 A1 | 10/2002 | Itoh |
| 6,758,573 B1 | 7/2004 | Thomas et al. | | 2003/0007887 A1 | 1/2003 | Roumpos et al. |
| 6,774,584 B2 | 8/2004 | Lys et al. | | 2003/0021117 A1 | 1/2003 | Chan |
| 6,777,891 B2 | 8/2004 | Lys et al. | | 2003/0039115 A1 | 2/2003 | Lin |
| 6,779,905 B1 | 8/2004 | Mazursky et al. | | 2003/0046842 A1 | 3/2003 | Maas et al. |
| 6,781,329 B2 | 8/2004 | Mueller et al. | | 2003/0057886 A1 | 3/2003 | Lys et al. |
| 6,783,117 B2 | 8/2004 | Wohrle | | 2003/0071932 A1 | 4/2003 | Tanigaki |
| 6,788,011 B2 | 9/2004 | Mueller et al. | | 2003/0076677 A1 | 4/2003 | Mohacsi et al. |
| 6,793,360 B2 | 9/2004 | Goslee | | 2003/0078791 A1 | 4/2003 | Tufte |
| 6,796,685 B1 | 9/2004 | Nemirow | | 2003/0095409 A1 | 5/2003 | Cheng |
| 6,801,003 B2 | 10/2004 | Schanberger et al. | | 2003/0137258 A1 | 7/2003 | Piepgras et al. |
| 6,802,635 B2 | 10/2004 | Robertson et al. | | 2003/0161139 A1 * | 8/2003 | Putallaz .................... 362/108 |
| 6,806,659 B1 | 10/2004 | Mueller et al. | | 2003/0209183 A1 | 11/2003 | Tufte |
| 6,815,724 B2 | 11/2004 | Dry | | 2003/0231488 A1 | 12/2003 | Albee |
| 6,817,731 B2 | 11/2004 | Tufte | | 2004/0066652 A1 | 4/2004 | Hong |
| 6,831,303 B2 | 12/2004 | Dry | | 2004/0070967 A1 | 4/2004 | Kennedy |
| 6,833,539 B1 | 12/2004 | Maeda | | 2004/0095078 A1 | 5/2004 | Leong |
| 6,837,591 B2 | 1/2005 | Tufte | | 2004/0095754 A1 | 5/2004 | Hsu |
| 6,840,646 B2 | 1/2005 | Cornelissen et al. | | 2004/0095780 A1 | 5/2004 | Reed |
| 6,848,822 B2 | 2/2005 | Ballen et al. | | 2004/0109317 A1 | 6/2004 | Ribarich |
| 6,851,844 B2 | 2/2005 | Guy | | 2004/0124790 A1 | 7/2004 | Han et al. |
| 6,854,208 B1 | 2/2005 | Chuang et al. | | 2004/0179358 A1 | 9/2004 | Tufte |
| 6,854,854 B2 | 2/2005 | Hoelen et al. | | 2004/0189218 A1 | 9/2004 | Leong et al. |
| 6,854,869 B1 | 2/2005 | Fernandez | | 2004/0232825 A1 | 11/2004 | Sorg |
| D503,467 S | 3/2005 | Flashinski et al. | | 2004/0246711 A1 | 12/2004 | Brenchley et al. |
| 6,869,202 B2 | 3/2005 | Tufte | | 2004/0257798 A1 | 12/2004 | Hart et al. |
| 6,869,204 B2 | 3/2005 | Morgan et al. | | 2004/0264185 A1 | 12/2004 | Grotsch et al. |
| 6,874,909 B2 | 4/2005 | Vanderschuit | | 2004/0264187 A1 * | 12/2004 | Vanderschuit .............. 362/235 |
| 6,880,948 B2 | 4/2005 | Koch et al. | | 2005/0024892 A1 | 2/2005 | Cabrera |
| 6,883,929 B2 | 4/2005 | Dowling | | 2005/0030747 A1 | 2/2005 | Bogdal |
| 6,883,931 B2 | 4/2005 | Tufte | | 2005/0036300 A1 | 2/2005 | Dowling et al. |
| 6,888,322 B2 | 5/2005 | Dowling et al. | | 2005/0047127 A1 | 3/2005 | Tutman |
| 6,890,085 B2 | 5/2005 | Hacker | | 2005/0074358 A1 | 4/2005 | Hart et al. |
| 6,897,624 B2 | 5/2005 | Lys et al. | | 2005/0099108 A1 | 5/2005 | Hofmann et al. |
| 6,902,301 B2 | 6/2005 | Kieronski | | 2005/0104503 A1 | 5/2005 | Ellens et al. |
| 6,921,184 B2 | 7/2005 | Tufte | | 2005/0128751 A1 | 6/2005 | Roberge et al. |
| 6,936,978 B2 | 8/2005 | Morgan et al. | | 2005/0162101 A1 | 7/2005 | Leong et al. |
| 6,951,401 B2 | 10/2005 | Van Hees et al. | | 2005/0169015 A1 | 8/2005 | Luk et al. |
| 6,952,079 B2 | 10/2005 | Shiang et al. | | 2005/0169643 A1 | 8/2005 | Franklin |
| 6,957,897 B1 | 10/2005 | Nelson et al. | | 2005/0169666 A1 | 8/2005 | Porchia et al. |
| 6,965,205 B2 | 11/2005 | Piepgras et al. | | 2005/0169812 A1 | 8/2005 | Helf et al. |
| 6,966,665 B2 | 11/2005 | Limburg et al. | | 2005/0173675 A1 | 8/2005 | Schmidt et al. |
| 6,976,774 B2 | 12/2005 | Reiss | | 2005/0174473 A1 | 8/2005 | Morgan et al. |
| 7,008,096 B1 | 3/2006 | Coushaine et al. | | 2005/0185392 A1 | 8/2005 | Walter et al. |
| 7,038,399 B2 | 5/2006 | Lys et al. | | 2005/0185398 A1 | 8/2005 | Scannell, Jr. |
| 7,046,920 B2 | 5/2006 | Flashinski | | 2005/0195598 A1 | 9/2005 | Dancs et al. |
| 7,052,152 B2 | 5/2006 | Harbers et al. | | 2005/0195600 A1 | 9/2005 | Porchia et al. |
| 7,067,981 B2 | 6/2006 | Nishio et al. | | 2005/0207152 A1 | 9/2005 | Maxik |
| 7,075,224 B2 | 7/2006 | Coushaine | | 2005/0213342 A1 | 9/2005 | Tufte |
| 7,080,932 B2 | 7/2006 | Keuper | | 2005/0258439 A1 | 11/2005 | Dry |
| 7,083,162 B2 * | 8/2006 | He et al. .................... 261/142 | | 2005/0258440 A1 | 11/2005 | Dry |
| 7,086,756 B2 | 8/2006 | Maxik | | 2005/0259416 A1 | 11/2005 | Gauna et al. |
| 7,086,767 B2 | 8/2006 | Sidwell et al. | | 2005/0265018 A1 | 12/2005 | Yasuda et al. |
| 7,093,958 B2 | 8/2006 | Coushaine | | 2005/0265023 A1 | 12/2005 | Scholl |
| 7,104,679 B2 | 9/2006 | Shin et al. | | 2005/0269581 A1 | 12/2005 | Dry |

| | | |
|---|---|---|
| 2005/0275626 A1 | 12/2005 | Mueller et al. |
| 2005/0281030 A1 | 12/2005 | Leong et al. |
| 2005/0285538 A1 | 12/2005 | Jaworski et al. |
| 2006/0001677 A1 | 1/2006 | Webb et al. |
| 2006/0002102 A1 | 1/2006 | Leonard |
| 2006/0002110 A1 | 1/2006 | Dowling et al. |
| 2006/0006784 A1 | 1/2006 | Takahara et al. |
| 2006/0022214 A1 | 2/2006 | Morgan et al. |
| 2006/0023447 A1 | 2/2006 | Justel et al. |
| 2006/0045818 A1 | 3/2006 | Moreland |
| 2006/0055315 A1 | 3/2006 | Bokor et al. |
| 2006/0071589 A1 | 4/2006 | Radkov |
| 2006/0081871 A1 | 4/2006 | Streubel |
| 2006/0082333 A1 | 4/2006 | Laski |
| 2006/0083013 A1 | 4/2006 | Wanninger et al. |
| 2006/0103291 A1 | 5/2006 | Ellens et al. |
| 2006/0114670 A1 | 6/2006 | Ho |
| 2006/0120080 A1 | 6/2006 | Sipinski et al. |
| 2006/0176690 A1 | 8/2006 | Yuen |
| 2006/0220990 A1 | 10/2006 | Coushaine et al. |
| 2006/0226795 A1 | 10/2006 | Walter et al. |
| 2006/0238136 A1 | 10/2006 | Johnson III et al. |
| 2006/0244000 A1 | 11/2006 | Jager et al. |
| 2006/0248783 A1 | 11/2006 | Lindquist et al. |
| 2006/0275040 A1 | 12/2006 | Franklin |

FOREIGN PATENT DOCUMENTS

| | | |
|---|---|---|
| WO | WO 03/026358 A1 | 3/2003 |
| WO | WO 2004/023850 A2 | 3/2004 |
| WO | WO 2004/068945 A1 | 8/2004 |
| WO | WO 2004/073399 A1 | 9/2004 |
| WO | WO 2005/086245 A2 | 9/2005 |
| WO | WO 2008/002427 A1 | 1/2008 |

OTHER PUBLICATIONS

PCT/US2007/021798, Written Opinion of the ISA.

* cited by examiner

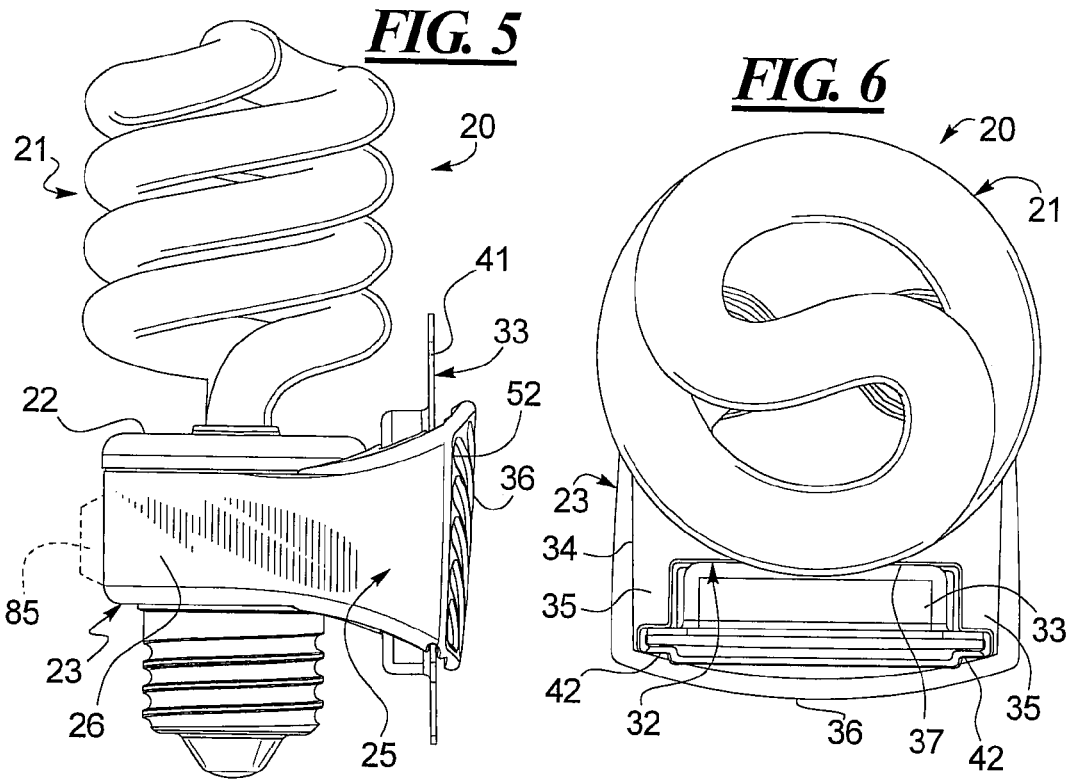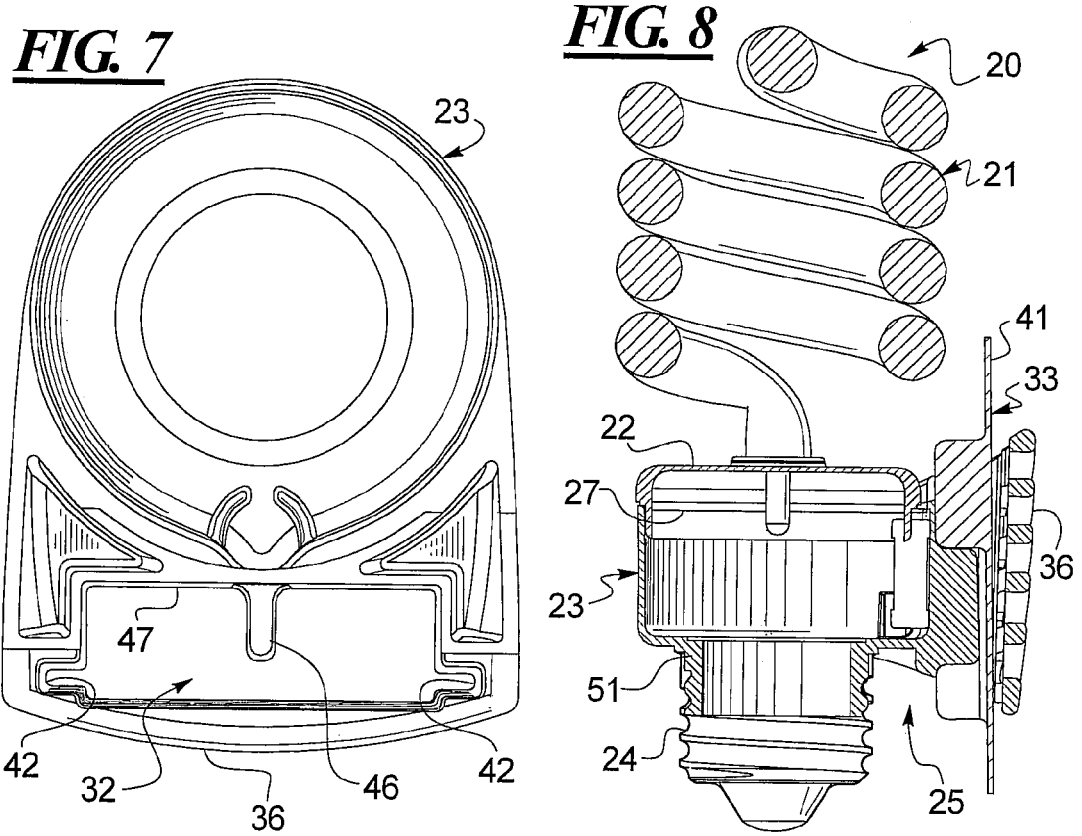

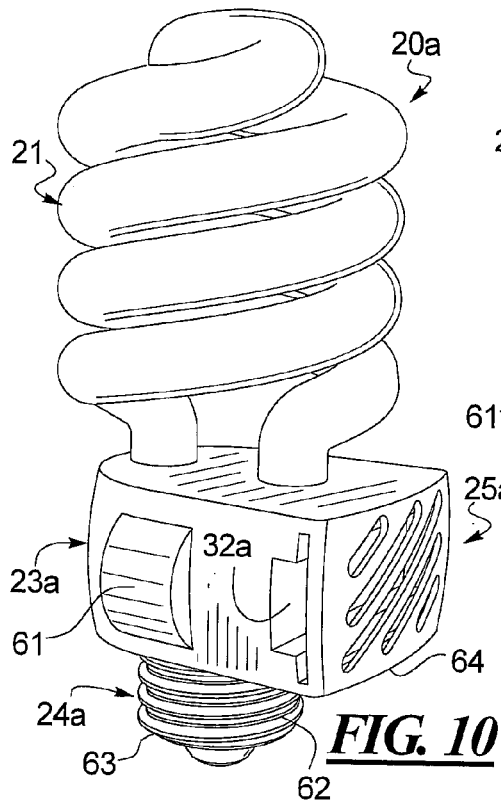
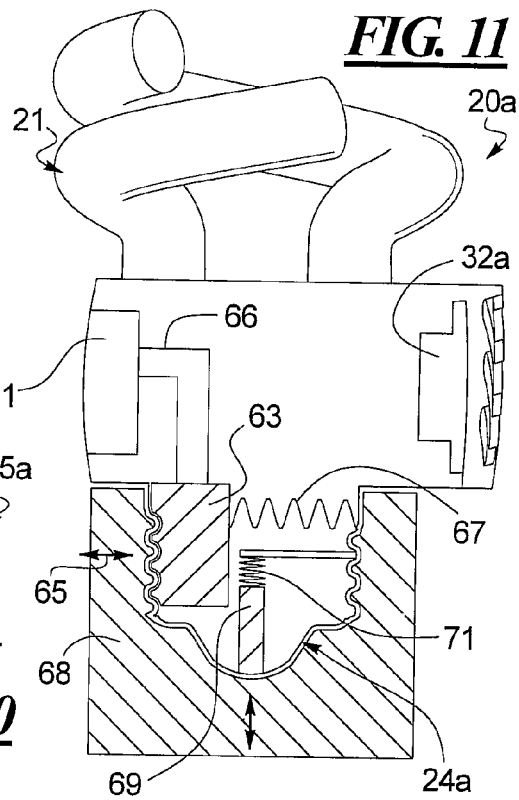
FIG. 10
FIG. 11
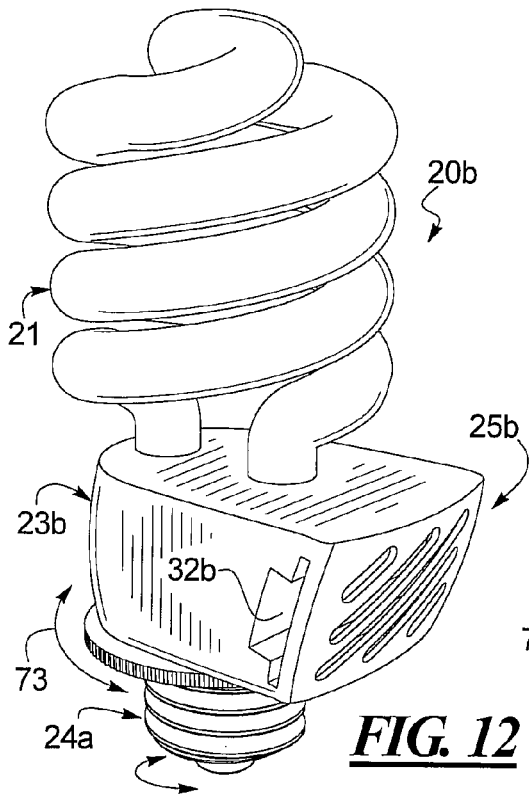
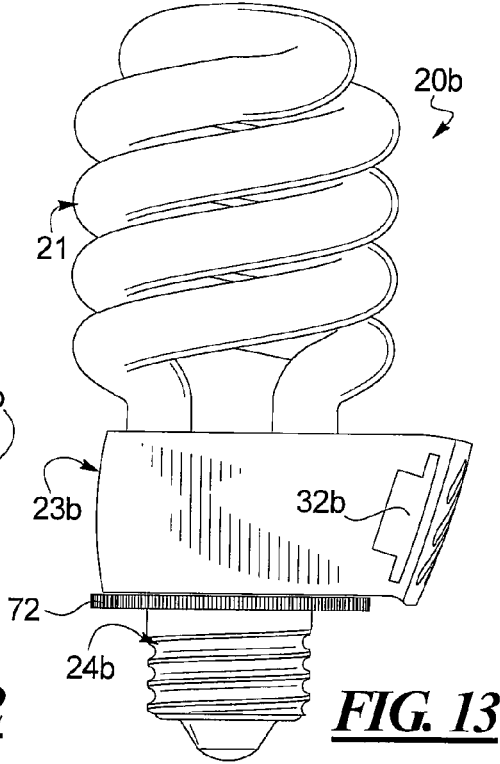
FIG. 12
FIG. 13

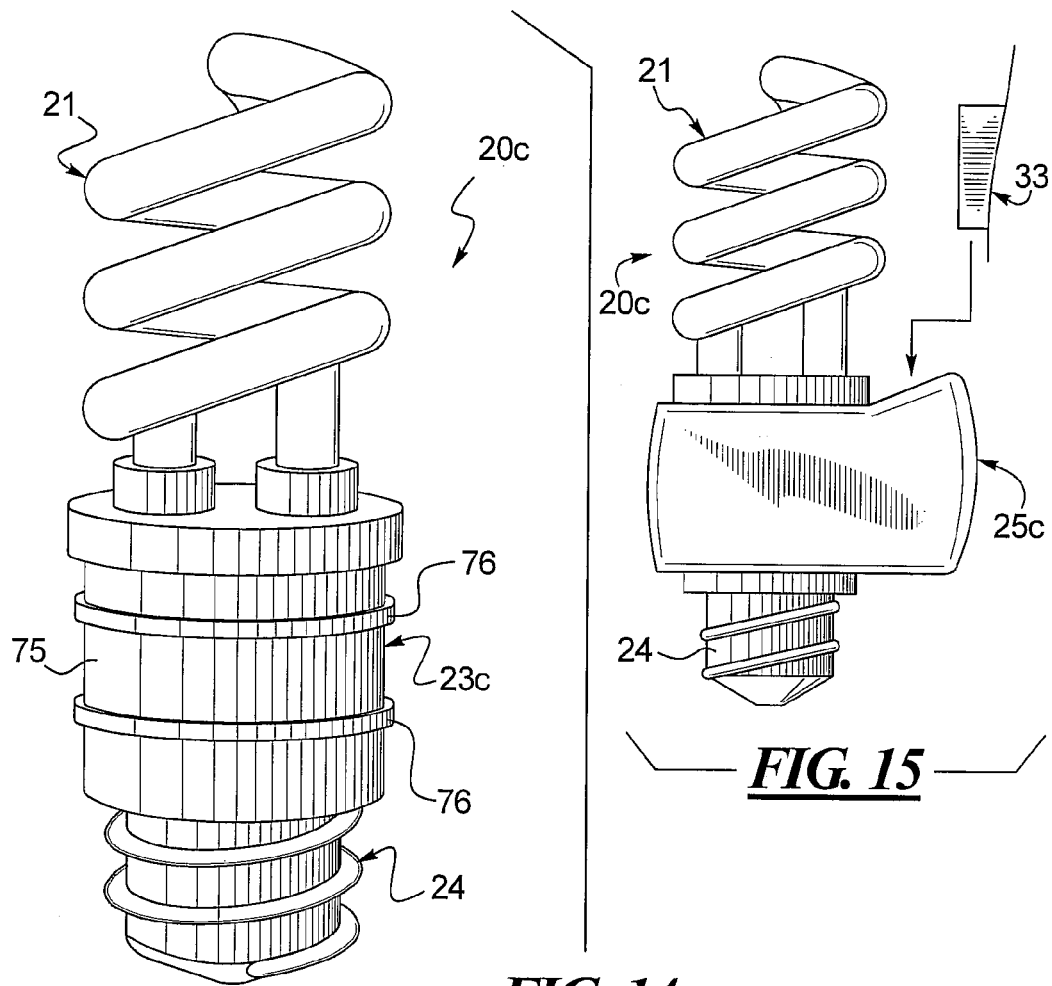
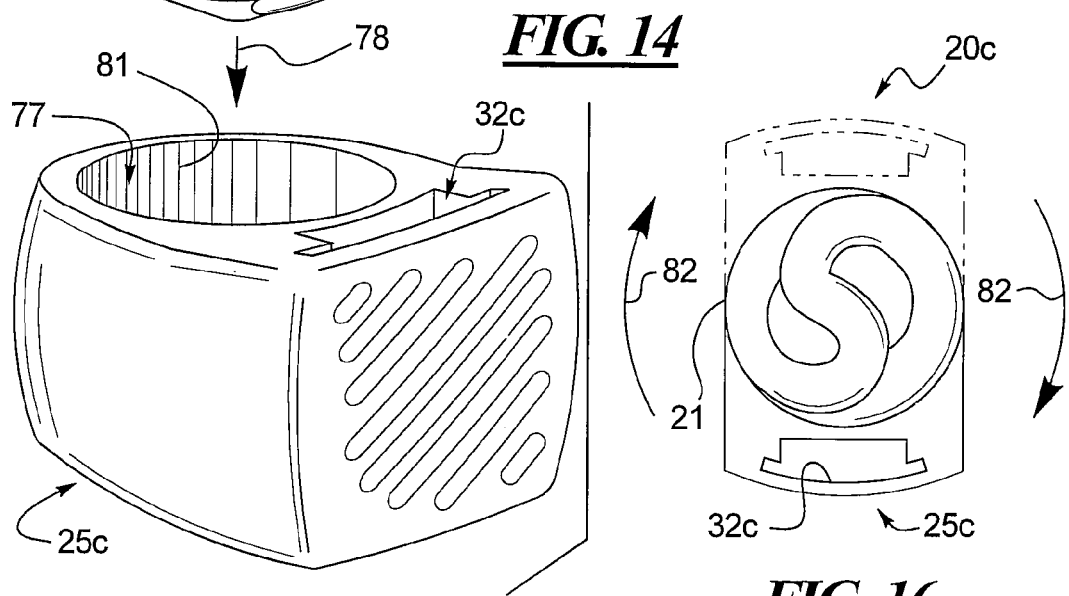
FIG. 14
FIG. 15
FIG. 16

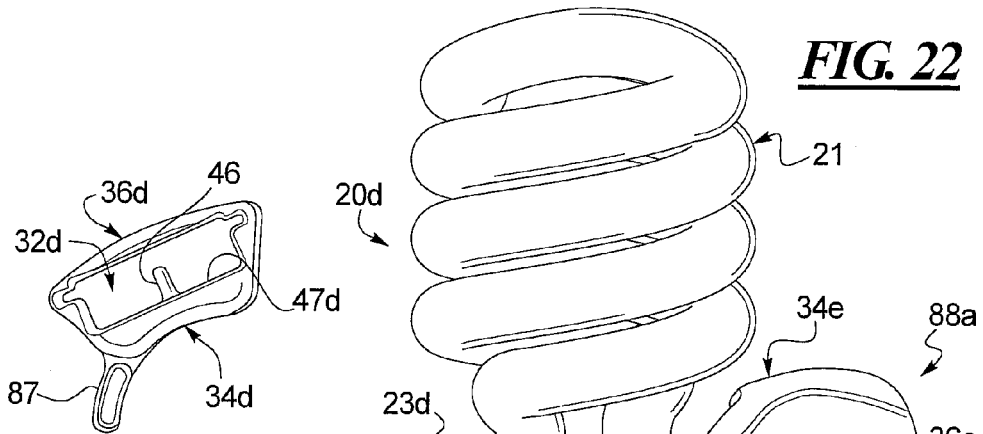
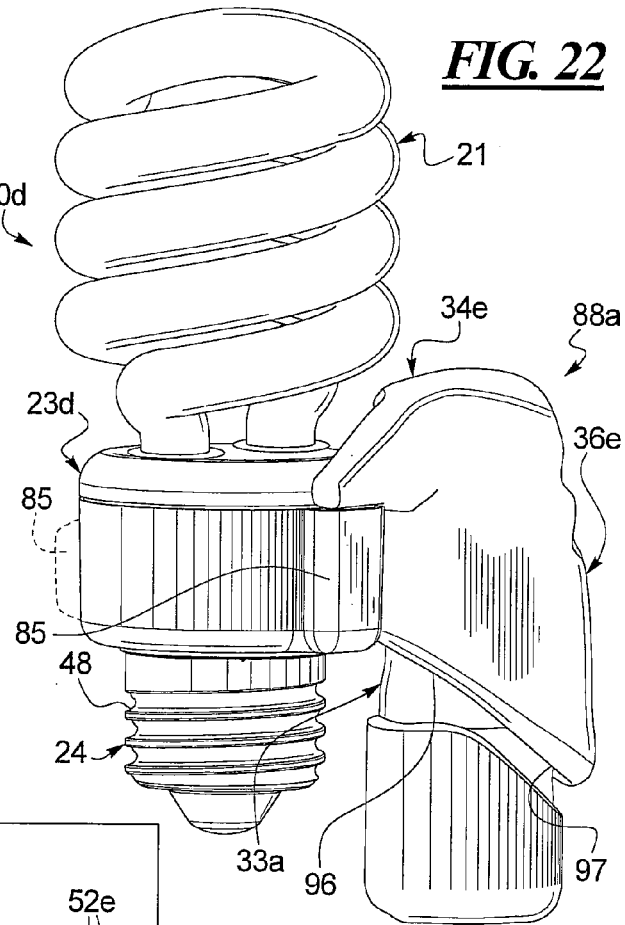
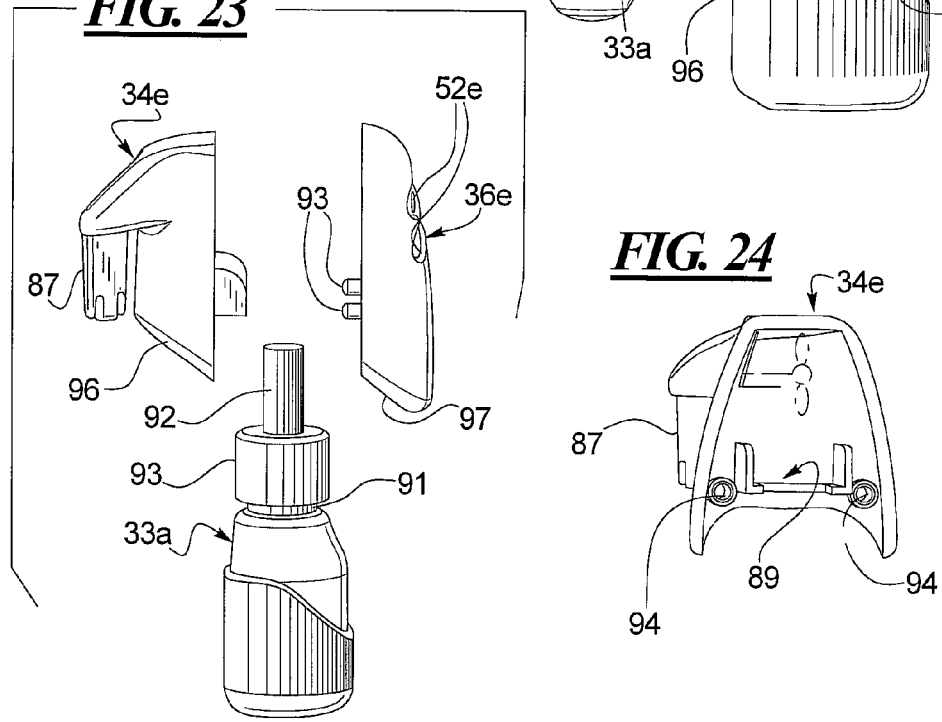

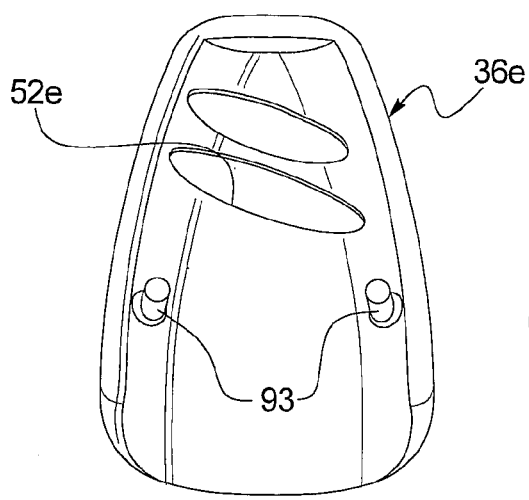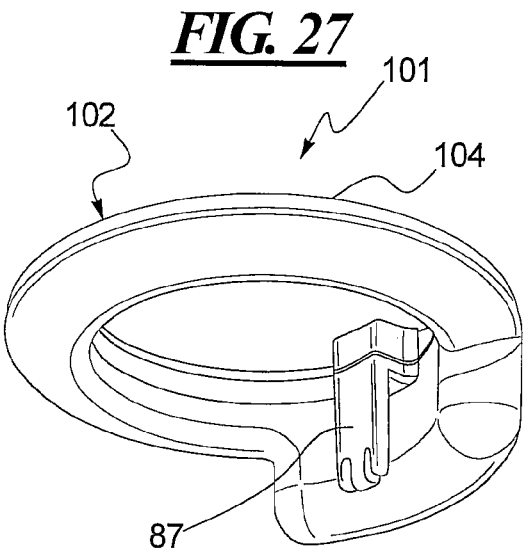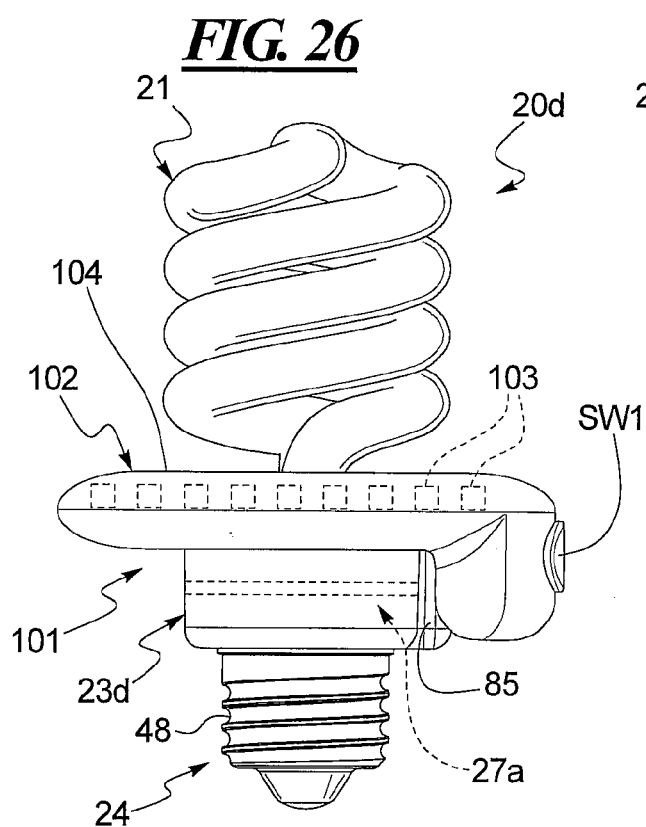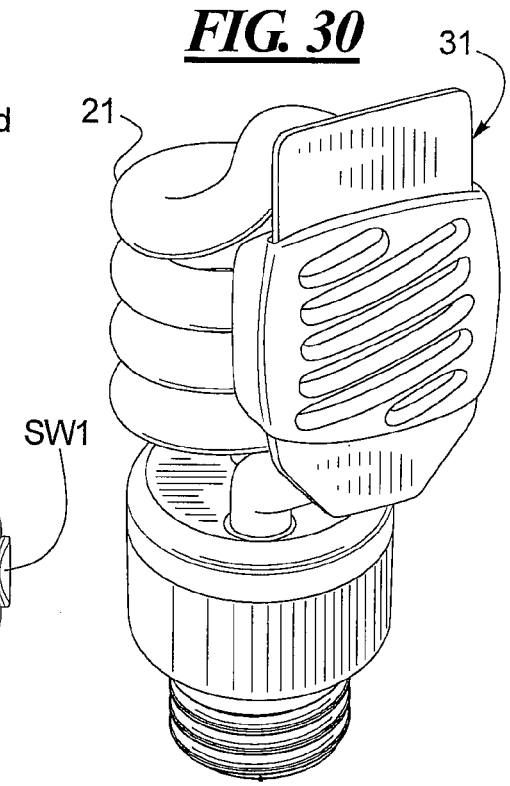

COMBINATION COMPACT FLOURESCENT LIGHT WITH ACTIVE INGREDIENT EMISSION

CROSS-REFERENCE TO RELATED APPLICATIONS

This application is a continuation-in-part of U.S. patent application Ser. No. 11/553,127, filed on Oct. 26, 2006, which is a continuation-in-part of U.S. patent application Ser. No. 11/426,055, filed on Jun. 23, 2006, which is a continuation-in-part of U.S. patent application Ser. No. 11/069,964, filed on Mar. 3, 2005, now U.S. Pat. No. 7,246,919, which claims priority to Provisional Patent Application Ser. No. 60/549,154, filed on Mar. 3, 2004. This application is also a continuation-in-part of U.S. patent application Ser. No. 10/561,822, filed on Jul. 2, 2004, still pending, which claims priority to Provisional Patent Application Ser. No. 60/483,913 filed on Jul. 2, 2003.

BACKGROUND

1. Technical Field

Substitutes for incandescent light bulbs are disclosed which provide energy-efficient emission of white light with a compact fluorescent light (CFL) and that also provide active ingredient vapor emission through a built-in dispenser. The disclosed light devices are used with conventional light sockets and the active ingredient is provided in the form of replaceable cartridges or containers.

2. Description of the Related Art

Creating a pleasant ambience is a popular aspect of home decor. This is often achieved through various combinations of fragrances. Lighting can also be combined with fragrance emission. For example, it is known to combine incandescent light bulbs with fragrance emission. Typically, heat from the light bulb is used to volatilize the fragrance material. Because heat from an incandescent bulb is relatively uncontrolled, the resulting fragrance emission is also uncontrolled. As a result, too much fragrance can be emitted and the fragrance can be used to quickly. Further, because fragrance materials can be flammable, the combination of an incandescent bulb and fragrance emission can present a fire safety issue.

Nightlight-type devices are also known which include fragrance dispensers. However, these devices are limited to use in bathrooms or on a wall with an electrical outlet. Because many homes do not include a sufficient number of electrical outlets, many consumers are reluctant to use them outside the bathroom. Further, while the utilitarian appearance of these devices in a bathroom is not bothersome to many consumers, their use outside of the bathroom, such as in a living room or family room, is not generally acceptable. Further, while nightlight-type fragrance dispensers may also provide light, because the devices are used in existing electrical outlets, they are generally positioned too low to provide effective lighting features, other than to operate as a nightlight. Conventional fragrance dispensers, such as plug-in diffusers, can provide pleasing aromas in a relatively inexpensive, compact package. However, as noted above with nightlight-type devices, such conventional fragrance dispensers generally take up outlets and are often located out of sight, causing a user to forget to adjust or refill the device.

Scented candles generate soft light and fragrance, thereby providing a pleasant mood. However, candles are a potential fire hazard and often produce unwanted smoke and wax drippings.

With growing concerns about energy costs and shortages, compact fluorescent lights (CFLs) are beginning to replace incandescent bulbs because they last longer and use a fraction of the energy consumed by incandescent bulbs. While CFLs are more expensive than incandescent bulbs, consumers save money over the life of a CFL because of the lower energy costs and longer operating life.

Further, numerous needs exist for the combination of ambient light with other volatile active emission other than fragrances such as air sanitization, air deodorization, the controlled release of insect repellent, insect attractant, insecticide, aromatherapy volatiles or other non-fragrant materials (any of which may be combined with fragrant materials if necessary to make the ambient environment more enjoyable or tolerable).

Therefore, there is a need for the combination of efficient white light emission, such as CFLs, with any one or more of the following: fragrance emission; air sanitization; air deodorization; insecticide emission; insect repellent emission; aromatherapy material emission; light emission that repels insects; light emission that attracts insects; and any combinations thereof.

SUMMARY OF THE DISCLOSURE

In view of the drawbacks of the lighting and fragrance devices currently available, devices are disclosed herein which provide various combinations of energy-efficient lighting and emission of volatile actives. The disclosed devices combine energy efficient white light emission and fragrance and/or volatile active emission without adding clutter to a room, without requiring the purchase of new fixtures, without taking up additional electrical outlets, without requiring aesthetically pleasing designs for the unit itself, and without presenting the fire hazards associated with open flames or fire hazards associated with active or fragrance emission that is driven by uncontrolled heat from an incandescent light bulb.

One disclosed substitute for a conventional light bulb includes a CFL with a specially equipped base structure disposed between the male connector and the coiled fluorescent tube. The modified base structure comprises an active vapor dispenser. In a refinement, the base includes a heater for increasing and/or controlling the rate of active vapor emission. The male connector may be a threaded male Edison-type connector or any other type of male connector for use with female light sockets. For example, a male connector may be a bayonet-type connector.

The placement of the active vapor dispenser in the base structure, or the structure disposed between the coiled fluorescent tube and the male connector, is ideal from active dispenser standpoint. If a heater is needed to control or increase active emission, access to power is conveniently provided in the middle base structure.

In a refinement, an active dispenser is not disposed in the base and/or is not an integral part of the base. Instead, a sidewall of the base comprises one or more electrical connection ports or outlets that enable the base to be connected to one or more different accessories that plug-in to the base. The plot-in accessories can include, but are not limited to a volatile active dispenser with a heater, a volatile active dispenser with a fan and a colored light emitting device, such as a device with an array of LEDs. The placement outlets on the base enables the consumer to change accessories or use multiple accessories. The plug-in accessories may also be combined with other non-electrical accessories, such as fragrance or active emitters that are mounted to or attached to the CFL tube.

Accordingly, in one refinement, an accessory that plugs into an outlet disposed on the base is a cartridge-type volatile active dispenser. Preferably, the dispenser includes a male connector that is received in the female outlet disposed on the base. Alternatively, the dispenser may be a bottle/wick-type dispenser used for emitting fragrance oils or other liquid actives. In such an embodiment, a fan may be employed to increase emission through the wick. Finally, a colored light accessory may plug into the female receptacle disposed on the base. In one embodiment, a LED/colored light show accessory is provided in the form of a ring that passes over the CFL tube and is supported on or above the base. In such an embodiment, the circuitry used to drive the CFL will also include circuitry used to drive the ring of LEDs will also include circuitry used to drive the LEDs and switch between pre-programmed colored light shows as disclosed fully in parent application Ser. Nos. 11/553,127, which is incorporated herein by reference.

In another refinement, permanently placing the active vapor dispenser in the base will typically cause the effective diameter of the base to increase. As a result, the outer diameter of the base may exceed the outer diameter of the coiled tube. Certain lamp designs may interfere with rotation of a wider base structure. As a result, partial disassembly of the lamp may be required to install a larger device. To alleviate this problem, three additional modified combination CFL/active vapor dispenser devices are disclosed.

One such device includes a CFL with a specially equipped base structure disposed between a modified threaded male connector and the coiled fluorescent tube. The modified male connector comprises two semi-cylindrical halves. One half of the male connector is fixed in position and includes outer threads or pins like a conventional male connector. The other half of the male connector is movable and can be pressed radially inward, against a spring bias, towards the other fixed half of the male connector. The movable half of the male connector includes threads or pins that match the threads or pins of the fixed half of the male connector when the movable half is biased outwards. When the movable half of the male connector is pressed inward towards the fixed half of the male connector, the effective outer diameter of the male connector is substantially reduced thereby enabling the connector to be stabbed into a conventional light socket without rotating the entire device. Release of the movable half of the male connector snaps both halves of the male connector into the light socket without rotation or with only minor amounts of rotation. Such a design is very convenient for use in certain lamp designs where the extra width of the base caused by the active vapor dispenser either prevents or inhibits rotation of the device when mating the male connector in the light socket.

The above design may be employed with Edison-type threaded connectors as well as non-Edison-type connectors that require at least some rotation to complete the connection. For example, the above design may be adapted for bayonet-type connectors which require the male connector to be rotated about 180°.

Further, the male connector may further comprise a spring-biased pin may extend downward between the two halves to increase the reliability of the electrical connection with the female socket.

Yet another combination CFL/active vapor emission device includes a modified male connector that is rotatable independent of the base structure that includes the active dispenser and that supports the coiled fluorescent tube. Specifically, a thumbwheel is provided at the underside of the base that is connected to the male connector. Rotation of the thumbwheel results in rotation of the male connector thereby enabling the device to be screwed into or inserted into a female socket without rotating the base or coiled tube.

Yet another combined CFL/active vapor dispenser comprises two parts: a modified CFL and a dispenser sleeve. The modified CFL includes a cylindrical base disposed between a male connector and a coiled fluorescent tube. The cylindrical base is axially received within the dispenser sleeve. In an embodiment, the cylindrical base and sleeve include electrical contacts for supplying power to a heater disposed in the dispensing sleeve. The dispensing sleeve is free to rotate about the cylindrical base. The dispensing sleeve includes a slot for accommodating an active cartridge or container and, as noted above, may include a heater for increasing or controlling active vapor emission. In another embodiment, a heater is disposed in the base as opposed to the dispensing sleeve thereby eliminating the need for an electrical connection between the cylindrical base and the sleeve. In either embodiment, because the CFL/cylindrical base/male connector is free to rotate with respect to the dispensing sleeve, the increased diameter presented by the dispensing sleeve will not interfere with certain lampshade designs and the device can be easily installed.

In a refinement, a disclosed substitute for a conventional light bulb that can be used indoors or outdoors and is configured to mate with a conventional light socket, provide white light with a CFL, fragrance emission and/or some sort of volatile active ingredient emission (e.g., insect repellent, insecticide, air sanitizer, air deodorizer, etc).

In a refinement, in addition to or instead of fragrance emission, the volatile actives control, attract, repel and/or terminate insects. The insect control functions may be combined with fragrance emission, a deodorizing function or an air sanitization function. Thus, in a refinement, the volatile active may provide a function selected from the group consisting of: insect control, insect termination, insect attraction, insect repellency, moth termination, fragrance emission, or deodorization, air sanitization, aromatherapy, volatile medicine emission and any combination thereof.

In a related refinement, a device made in accordance with this disclosure can release an active that repels insects, such as mosquitoes, to either keep such insects out of a home or to keep such insects away from an outdoor area such as a patio or porch. The active can repel or kill the problematic insects. In the alternative, the disclosed devices may be used to attract insects and keep them away from an outdoor area such as a porch or deck. Indoor applications include the use of a disclosed device in a closet that emits a volatile active that kills moths and further that emits energy efficient white light.

Thus, the combination CFL/active emitter device disclosed herein can be used in porch/deck lighting systems and outdoor perimeter lighting systems.

Preferably, the fragrance or active delivery may be provided by scented oil or scented gels provided in cartridges which may be removably secured in/to the device, at the base of the device disposed between the male connector and the coiled CFL tube to provide the desired fragrance emission. This allows a user to change between different fragrances and/or replace empty cartridges, without the need to change the entire bulb device. The convenient means for replacing an active cartridge is important as many CFLs are designed to last multiple years. Active cartridges or containers, such as fragrance cartridges, are not intended to last that long and will need to be replaced substantially more frequently.

In another refinement, a refill cue may be provided by the circuitry of the device that informs the user when the active or fragrance has become depleted and when a refill cartridge or bottle is needed.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein:

FIG. 5 is a side plan view of the device shown in FIGS. 1-4.

FIG. 6 is a top plan view of the device shown in FIGS. 1-5.

FIG. 7 is a bottom plan view of the shell of the base structure of the device shown in FIGS. 1-6.

FIG. 8 is a side sectional view of the device shown in FIGS. 1-7.

FIG. 10 is a perspective view of an alternative combination CFL/active vapor emission device with a modified connector enabling the device to be snapped into a female socket without rotating the device.

FIG. 11 is a partial sectional view of the base and threaded male connector of the device shown in FIG. 10 as received into a threaded socket.

FIG. 12 is a perspective view of yet another alternative combination CFL/active vapor emission device with a rotatable electrical connector that enables the device to be connected to a threaded light socket without rotating the upper portion of the device.

FIG. 13 is a partial side view of the device shown in FIG. 12.

FIG. 14 is an exploded view of an alternative CFL lamp that can be inserted axially into an active vapor dispensing sleeve.

FIG. 15 is a side plan of the assembled device shown in FIG. 14 further illustrating the placement of an active cartridge into the dispensing sleeve.

FIG. 16 is a top plan view of the device shown in FIGS. 14-15 illustrating the rotatability of the dispensing sleeve with respect to the CFL.

FIG. 21 is a bottom plan view of the cartridge holder shown in FIG. 20.

FIG. 22 is a side plan view of a modified CFL connected to a volatile liquid dispenser.

FIG. 23 is an exploded view of the volatile liquid dispenser and volatile liquid container/wick.

FIG. 24 is a front plan view of the inner half of the container holder shown in FIGS. 22 and 23 that includes the male electrical connector.

FIG. 25 is a real plan view of the vented outer half of the container holder shown in FIGS. 22 and 23.

FIG. 26 is a side plan view of a modified CFL connected to an LED/colored light show accessory.

FIG. 27 is a bottom perspective view of the LED/colored light show accessory shown in FIG. 26.

FIG. 30 is a perspective view of a volatile active cartridge clip that may be attached to a CFL tube for use in conjunction with other embodiments shown herein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Turning to FIGS. 1-8, a device 20 is illustrated that provides energy efficient white light with a CFL 21 that is mounted to and extends upward from a top panel 22 of a base structure 23. The base structure 23 is disposed between the CFL 21 and a male connector 124 that, in this case, is a threaded male connector, typically referred to as an Edison-type male connector or an Edison connector.

Figure 4:
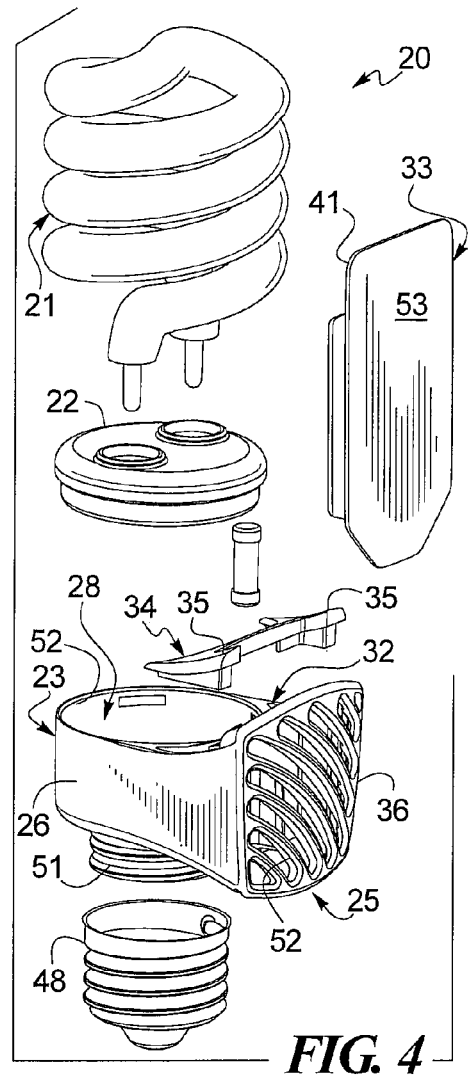
FIG. 4 is an exploded view of the device shown in FIGS. 1-3.

The base 23 further comprises an active ingredient dispenser or volatilizer 25. The dispenser 25 may be integral with the base 23 as illustrated in FIG. 4 or the dispenser 25 may be connected to an outer surface 26 of the base 23 (see also FIGS. 17-21 below). The top panel 22 of the base 23 provides support for the CFL 21 and also houses a board 27 (FIG. 8) disposed in the compartment 28 (FIG. 4) of the base 23. The board 27 accommodates the circuitry 31 (FIG. 9) that includes the electronics for operating the CFL 21 and a heater for supplying heat to the active dispenser 25.

As seen in FIGS. 1-2 and 4-5, the dispenser 25 includes a slot 32 for receiving an active cartridge 33. In the embodiment 20, the base 23 also includes a frame 34 which includes two forwardly extending tabs 35 that engage the grill 36 (FIGS. 4 and 6). The frame 34 includes a rear wall 37 that extends between the tabs 35. As seen in FIG. 6, the tabs 35 and rear wall 37 of the frame 34 define a top opening of the slot 32 for accommodating the cartridge or container 33.

Figure 1:
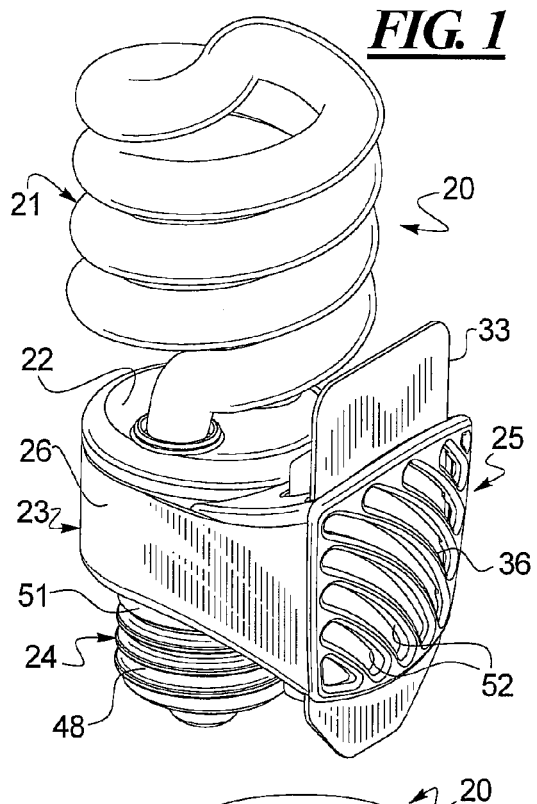
FIG. 1 is a perspective view of a disclosed combination CFL/active vapor emission device with a threaded, screw-in base.
Figure 3:
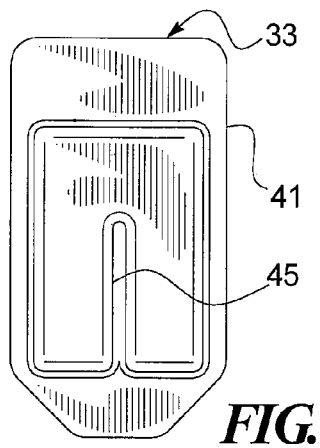
FIG. 3 is a real plan view of a replaceable cartridge used with the device shown in FIGS. 1-2.
Figure 2:
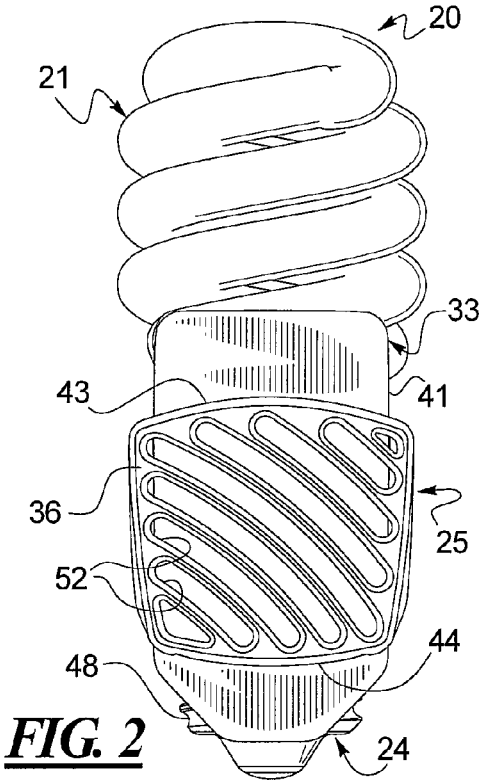
FIG. 2 is a front plan view of the device shown in FIG. 1.

As shown in FIG. 7, the slot 32 further extends between the grill 36 in the rear wall 47 of the base structure 23. The cartridge 33 includes a continuous outer flange 41 that is frictionally received within the side slots 42 formed behind the grill 36 (FIG. 7) of the base structure. As shown in FIG. 2, the grill 36 is tapered it extends downward from the top 43 to the bottom 44. Further, as seen in FIGS. 3 and 7, the cartridge 33 includes a vertical slot 45 which receives the pin 46 that extends outward from the rear wall 47 of the slot area 32. The pin 46 serves as a stop to prevent further downward movement of the cartridge 33. Accordingly, in the embodiment illustrated in FIGS. 1-8, the cartridge 33 must be inserted and removed through the top of the slot 32 or behind the top 43 of the grill 36.

The grill 36 further includes a plurality of openings 52 to facilitate the passage of active vapor through the grill 36. The front panel 53 of the cartridge 33 may be a porous membrane that permits vaporized active to pass through the panel 53 and through the openings 52 of the grill 36. As noted above, the device 20 may be equipped with a heater to facilitate this process.

As seen in FIG. 4, an Edison-type male connector 24 with a threaded metal shell 48 provides power to the device 20. The connector 24 may be threadably connected to the base 23 at the lower threaded extension shown at 51. The top panel 22 of the base structure 23 may be connected to the cylindrical opening 52 by conventional means such as a snap-fit, adhesive or welding.

Figure 9:
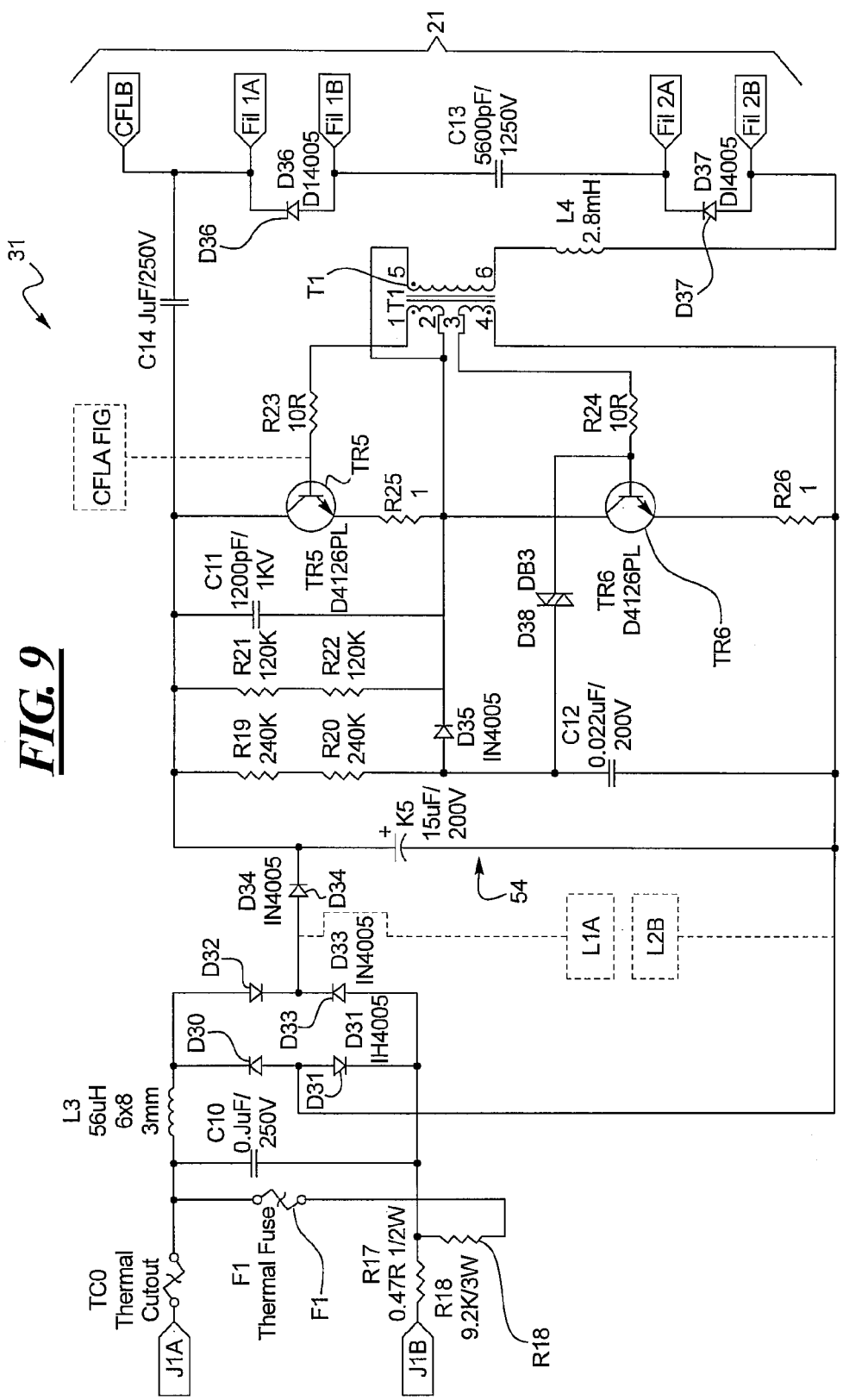
FIG. 9 is a schematic diagram illustrating the circuitry for the CFL and optional cartridge heater for the device shown in FIGS. 1-8.

Turning to FIG. 9, the heater for the fragrance cartridge 33 and dispenser 25 is shown at R18 and F1. The circuitry 31 is standard CFL circuitry and will not be described in detail here. The four diodes D30-D33 shown in the upper left of FIG. 9 act as a rectifier and convert the 110V input to DC voltage which is delivered to the CFL ballast circuitry 54 through the diode D34. The ballast circuitry 54 includes the two transistors TR5 and TR6 which form an oscillating circuit with the transformer T1 to convert the DC voltage to 350V AC which is sent to the diodes D36 and D37 and on to the CFL 21 (see Fil 1A-1B, Fil 2A-2B on the right side of FIG. 9).

Alternative devices ate shown at 20a, 20b, 20c in FIGS. 10-11, 12-13 and 14-16 respectively. These devices are designed to facilitate installation in lamps which may include wire supports or frames for supporting a lampshade that may interfere with rotation of a base structure 23, which is wider than in incandescent bulb due to the incorporation of the active dispenser 25.

Turning to FIGS. 10-11, the device 20a includes a base 23a that features a button or actuator 61. The male connector 24a comprises two semi-cylindrical halves 62, 63. The half 62 is fixedly connected to the underside 64 of the base 23a and remains stationary with respect to the base 23a. On the other hand, the half 63 is movable in both directions indicated by the arrow 65 and FIG. 11. As shown in FIG. 11, the actuator 61 is linked or connected to the connector half 63 by a linkage or connection mechanism 66, the details of which are not important and therefore the connection 66 is shown only schematically in FIG. 11. A spring or biasing means 67 is used to bias the connector half 63 towards a fully extended position as shown in FIG. 10. To reduce the effective outer diameter of the connector 24a which thereby enables the connector 24a to be inserted into the female socket 68 (FIG. 11) without rotating the connector 24a or the device 20a, the actuator 61 is used to move the connector half 63 towards the right in FIG. 11. With the reduced size of the connector 24a as shown in FIG. 11, the connector 24a may be inserted downwardly or stabbed into the socket 68 without rotation or with only minor amounts of rotation. Release of the actuator 61 results in the connector half 63 returning to its extended position as shown in FIG. 10 under the bias of the spring 67. As a result, the connector 24a essentially snaps into place in the female socket 68.

While the connector 24a and socket 68 is illustrated in FIG. 11 are threaded or modified-Edison connectors, the concepts disclosed in the device 20a can be employed in other types of connectors, such as bayonet-type connectors, that are rotated in order to make the electrical connection. As shown in FIG. 10, the base 23a is wider than a corresponding section of a conventional incandescent light bulb. Because some lamps may be designed with wire supports or frames for supporting a lampshade immediately above the lamp socket 68, the device 20a cannot be used with some lamps or may require partial disassembly lampshade support prior to installation of the device 20a. Obviously, this is inconvenient and the stab-in procedure shown in FIGS. 10-11 avoids this problem. To facilitate or ensure a proper electrical connection is made, the connector 24a may be equipped with a downwardly extending pin 69 that is biased downward by the spring 71. The device 20a of FIGS. 10-11 also includes a transverse slot 32a for the active dispenser 25a.

FIGS. 12-13 illustrate another embodiment 20b with a male connector 24b that is rotatable with respect to the base 23b. The connector 24b comprises a thumbwheel 72 that can be used to rotate the connector 24b in either direction is indicated by the arrow 73. Because the connector 24b can rotate independent of the base 23b, the device 20b can be easily installed in tight environments as the base 23b and CFL 21 do not need to be rotated.

FIGS. 14-16 illustrate yet another embodiment 20c which includes a modified base 23c having a cylindrical sidewall 75 with one or more circular electrical connectors 76. A standard male connector 24 is employed. The sidewall 75 of the base 23c fits downward through the cylindrical opening 77 of the active dispenser 25c as indicated by the arrow 78. The inner wall 81 of the dispenser 25c comprises electrical connectors for engagement with the electrical connectors 76 of the base 23c. The connectors 76 can be used to provide power to a heater disposed in the dispenser 25c. The dispenser 25c is held in place on the cylindrical wall 75 of the base 23c by friction or other means. However, the dispensing sleeve 25c can rotate with respect to the base 23c and therefore the CFL 21, base 23c and male connector 24 may be rotated while the sleeve dispenser 25c is held in place while a connection with a female socket is established. Further, as shown in FIG. 16, the dispensing sleeve 25c may be rotated after it is installed on the CFL 21 as indicated by the arrows 82, which may facilitate replacement of the cartridge 33.

The cartridge containers 33 may be provided in almost any form that can be inserted into the slots 32, 32a, 32b, and 32c. Another option is to utilize a solid mat-type structure or substrate that is impregnated with insect control material as disclosed, for example, in commonly assigned U.S. Pat. Nos. 7,046,920 and 6,551,560, both of which are incorporated herein by reference. One type of exemplary cartridge 32 is disclosed in U.S. Pat. No. 4,849,606 and, as another alternative, impregnated substrates such as "sand core" tablets or other types of structures as disclosed in "WO 2004/068945 maybe employed. Both of these references are also incorporated herein by reference. The active may also be impregnated into thin sheets of paper or other substrates that may be transparent, translucent or opaque. Honeycomb structures, such as cardboard honeycomb structures impregnated with active material may also be employed. Finally, as shown in FIGS. 22-25 bottle-type containers may be used as well.

Figure 17:
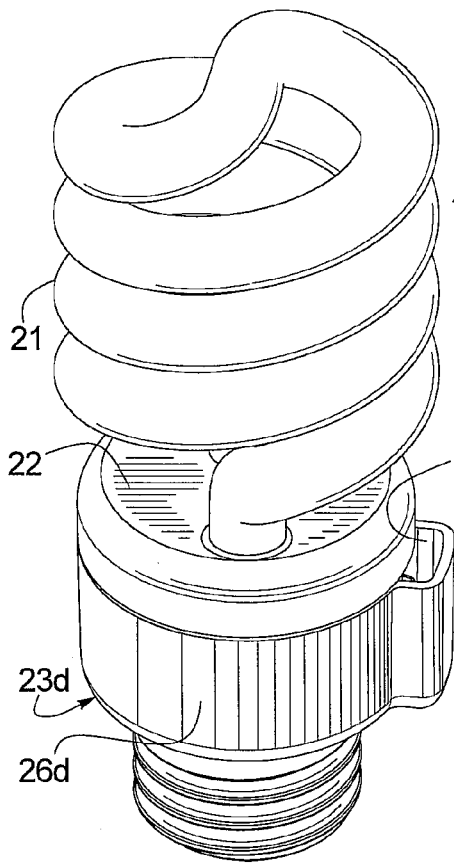
FIG. 17 is a top perspective view of a modified CFL which includes a female electrical connector on its base for receiving a male electrical connector of an accessory, such as the volatile active cartridge accessory of FIG. 19, the volatile active bottle accessory of FIG. 22, and/or the LED accessory of FIG. 26.
Figure 19:
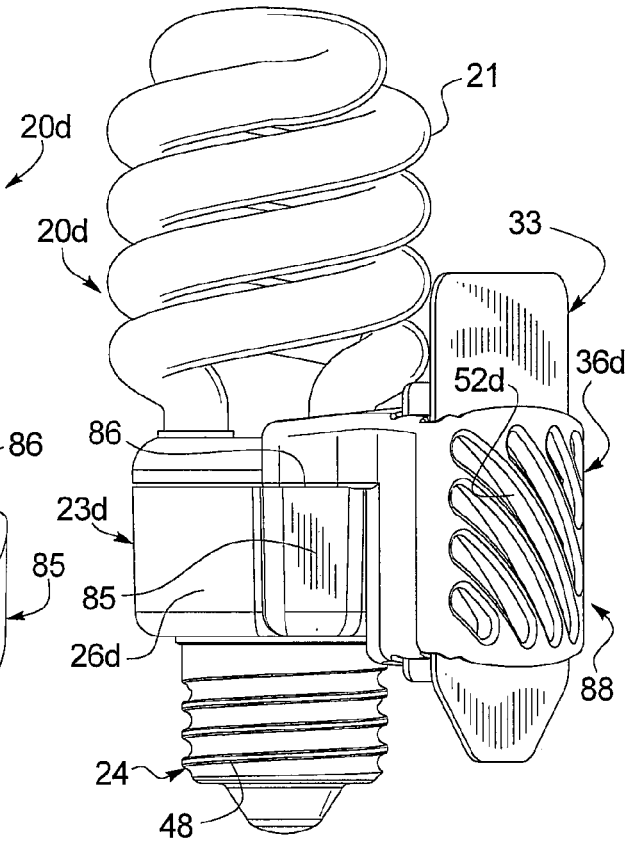
FIG. 19 is a side plan view of the modified CFL of FIG. 17 connected to a volatile active cartridge accessory.
Figure 18:
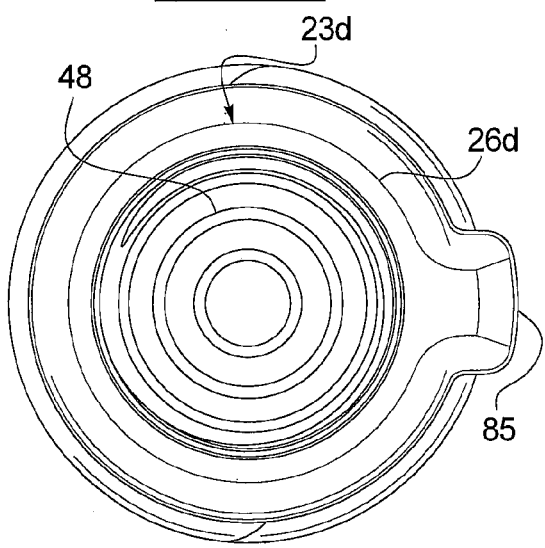
FIG. 18 is a bottom plan of the modified CFL of FIG. 17.
Figure 20:
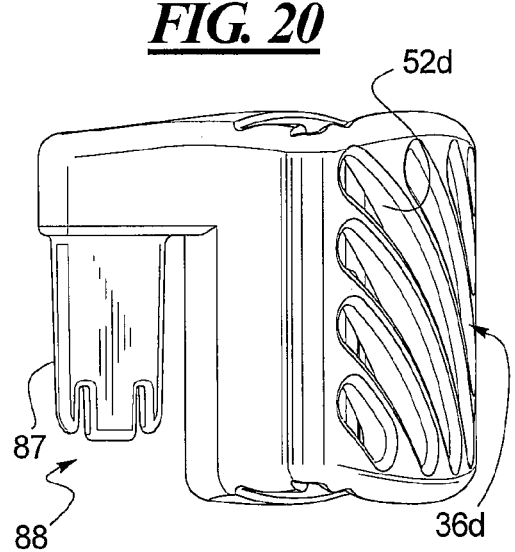
FIG. 20 is a perspective view of the cartridge holder shown in FIG. 19.

Turning to FIG. 17, a modified CFL device 20d is shown with a coiled tube 21 connected to a top panel 22 of a modified base 23d. As shown in FIGS. 17-18, the modified base 23d includes a female electrical receptacle 85 is mounted to the outer surface 26d of the base 23d. The receptacle 85 includes an upper opening 86 that receives a male plug such as the one shown at 87 in FIG. 20 which is part of the detachable active cartridge dispenser 88. FIG. 19 illustrates the dispenser 88 mounted on the device 20d. The female socket 85 provides power to the dispenser 88, which may be equipped with a heater (not shown) as discussed above. As shown in FIGS. 20-21, the dispenser 88 includes a front grill 36d with the vents 52d that is attached to a rear frame 34d. The rear frame 34d is connected to the male plug 87 and includes the rear wall 47d from which the post 46d extends in a manner similar to the embodiment shown in FIG. 7. The slot 32d therefore includes the same features as the slot 32 of FIG. 7.

In FIG. 22, the device 20d is connected to a volatile active dispenser 88a designed to accommodate a bottle-type container 33a as opposed to a cartridge-type container 33 described above. The bottle 33a is ideal for liquid active materials as opposed to gel active materials. The dispenser 88a comprises two halves including a rear frame 34e and a front grill 36e. As seen in FIG. 24, the rear frame 34e includes a support bracket 89 for accommodating the bottleneck or slot 91 (FIG. 23) of the container 33a. The wick 92 extends upward from the top or cover 93 is disposed in general alignment with the vents 52e when the container 33a is received in the dispenser 88 as shown in FIG. 22. The grill/cover 36e includes a pair of posts 93 that are frictionally received in the apertures 94 of the rear frame 34e. To replace the container 33a, the cover 36e is detached from the rear frame 34e and the new container 33a is placed onto the bracket 89 before the cover 36e is replaced.

Turning to FIGS. 26-27, the device 20d may also be connected to a LED/colored light show accessory 11. An accessory 101 includes a ring-shaped housing 102 which covers a circular array of LEDs 103 shown in phantom in FIG. 26 and disposed above the circuit board 27a. Power to drive the LEDs is provided through the male plug 87 (FIG. 27) which is received in the female socket 85 (FIG. 26). An activation or toggle switch is shown at SW1.

Figure 28:
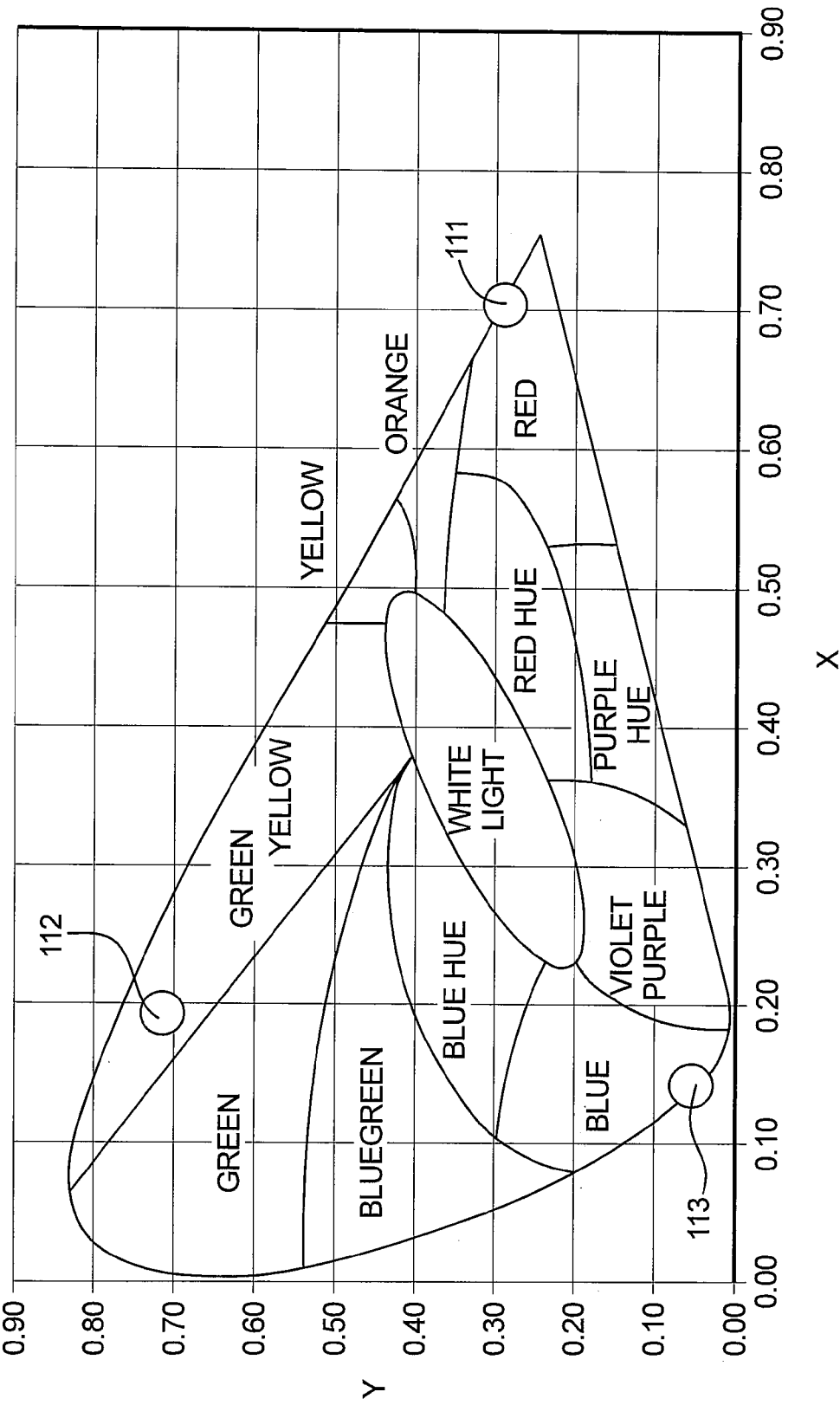
FIG. 28 is an exemplary CIE chart with three coordinates corresponding to three LEDs of different colors, red, green and blue, wherein a colored light show presented in accordance with this disclosure comprises any path disposed within the boundaries of the curve carried out over time.

The operation of the LED accessory 102 will be described in connection with FIGS. 28-29. Turning to FIG. 28, the intensity and exact color of the light emitted from the adapter accessory 101 may be varied by changing the current applied to each diode. The different combinations of LED operations will alter the perceived color when the light from the LEDs 103 is diffused to form one perceived color. This is best understood in connection with the exemplary CIE chart of FIG. 28 with three coordinates corresponding to three colored (red 111, green 112 and blue 113) LEDs. The colored light show as described herein includes starting and ending color points and proceeding along any predefined path between those two points during the course of a show.

A color point refers to the settings of the LEDs 103 at a given moment of the colored light show, which provides a specific perceived color. As the settings of the LED array 103 change over time in accordance with the instructions for the colored light show, the color points can ultimately be perceived as a "wash" or "waves" of colors. Because we are discussing "perceived" colors, the starting color point does not directly correspond to the wavelengths of light emitted by the LEDs 103 used in the color light show, inasmuch as those wavelengths are substantially constant. The starting and ending color points can, however, be defined by coordinates on the CIE chart of FIG. 28.

The color points can also be defined by the relative intensities of the lights emitted from the LEDs 103 used to produce the color light show (e.g., the operational settings for the different LEDs 103 at specified points of the colored light show). For instance, a color point can be defined by the specific intensity level set at that point in time for each LED 103 being used, and the dominant wavelength of each LED 103. Preferably, intensity levels will be defined by the pulse widths of the LEDs 103 (e.g., as a percentage of full intensity of the LEDs 103).

It will be understood by one of ordinary skill in the art that the combination of the lights from different-colored LEDs 103 at specified intensities will directly correspond to a set point on the CIE chart. Therefore, the different possible methods discussed above for defining the color points (e.g., using CIE chart coordinates or specific LED 103 settings) are substantially equivalent for purposes of defining a perceived color.

It will be noted, however, that there are many ways in which the lights from the different LEDs 103 can be combined. In some methods, especially where a diffuser 104 is not used and the LEDs 103 are merely placed in close proximity to each other, a user may perceive different colors close to the emission points of the LEDs 103. Color points, as discussed herein, refer to the color of a substantially complete mixture of the lights from the different LEDs 103, even though there may be observable portions of the display in which the user sees distinct colors corresponding to the wavelengths from the individual LEDs 103, rather than the complete mixture.

The starting and ending color points are similar to the first and last entries in a look-up table setting forth all of the points of a color show in a conventional system; however, instead of providing all of the intervening points from the conventional look-up table, the LED/colored light show accessory 101 can dispense with the need to determine and store each and every intervening color point. To achieve this effect, the above-referenced timing information is provided. The timing information defines timing aspects of the colored light show and LED 103 control.

Using the timing information, a microprocessor U1 (FIG. 29) may calculate all of the intervening color points for the colored light show on its own. This saves valuable memory space that would otherwise have to be devoted to complex look-up tables for various colored light shows. The timing information preferably includes information concerning the duration of the show, from display of the starting color point to the ending color point. The timing information also preferably includes information concerning the ramp speed for the LEDs 103, either as a whole, or individually. The ramp speed refers to the speed of intensity change of the LEDs 103. Generally, ramp speed may be defined as the unit of time it takes the LED 103 to change one intensity level (for that particular show), with each intensity level being equal. This can also be defined as the change of intensity per unit of time.

The LEDs 103 may be controlled by pulse width modulation (PWM) such that the pulse width of a constant current applied for a portion of the duty cycle is varied to alter the intensity of the light emitted from the LED 103. The intensity level of the LED 103 can be measured as a fraction of the duty cycle during which the constant current is applied, which, among other ways, can be expressed as a percentage. When an LED 103 is not on, the pulse width is at 0%. When a constant current is applied to the LED 103 for half of the duty cycle, the intensity of the LED is at 50%. Ramp speed may be defined as the amount of time between changes of intensity of one percentage point of total intensity. Consequently, if the ramp speed of an LED 103 is set at two seconds, then during the course of the colored light show that LED 103 will change its intensity by one percentage point every two seconds until reaching the target value (i.e., the intensity value of the LED 103 for achieving the ending color point). In an embodiment, ramp speed is defined as the percentage change per second.

Of course, the speed can be defined in any one of a number of ways, as would be understood by one of ordinary skill in the art. Also, the ramp speed can be a positive or negative value, depending on whether the intensity of the LED 103 is to be increased or decreased during the colored light show. Alternatively, a microprocessor U1 can be programmed to increase or decrease the intensity setting by comparing the starting intensity setting to the ending intensity setting. Thus, for instance, if the microprocessor U1 determines that the value of the ending setting is lower than the value of the starting setting, the microprocessor U1 will decrease the intensity of the LEDs 103 at a rate set by the given ramp speed.

With the timing information provided, the microprocessor 103 controlling the LEDs 103 may be provided with logic that calculates the intervening color points between the starting and ending points of the CIE chart of FIG. 28. The logic reads the timing information from memory (not shown) and adjusts the duty cycle for each LED 103 in accordance with the ramp speed and target intensity. The intensity for each LED 103 is adjusted until the target value is reached or the duration of the show has been reached. At this time, the microprocessor U1 will read the next set of timing information from memory and begin again. Of course, if the target intensity is reached prior to the duration of the show, the microprocessor U1 will hold the intensity of the LED 103 until the duration is reached. If a continuously changing show is desired, the ramp speed may be set such that the target intensity is not reached prior to the duration of the show and thus, the target value will never be reached. Likewise, the microprocessor U1 may be configured to ignore the duration, and load the next intensity and ramp speed as soon as the target intensity is reached.

The programming for achieving this would be readily understood by one of ordinary skill in the art. Accordingly, a detailed description of the many different ways of programming the microprocessor U1 will not be provided herein.

Figure 29:
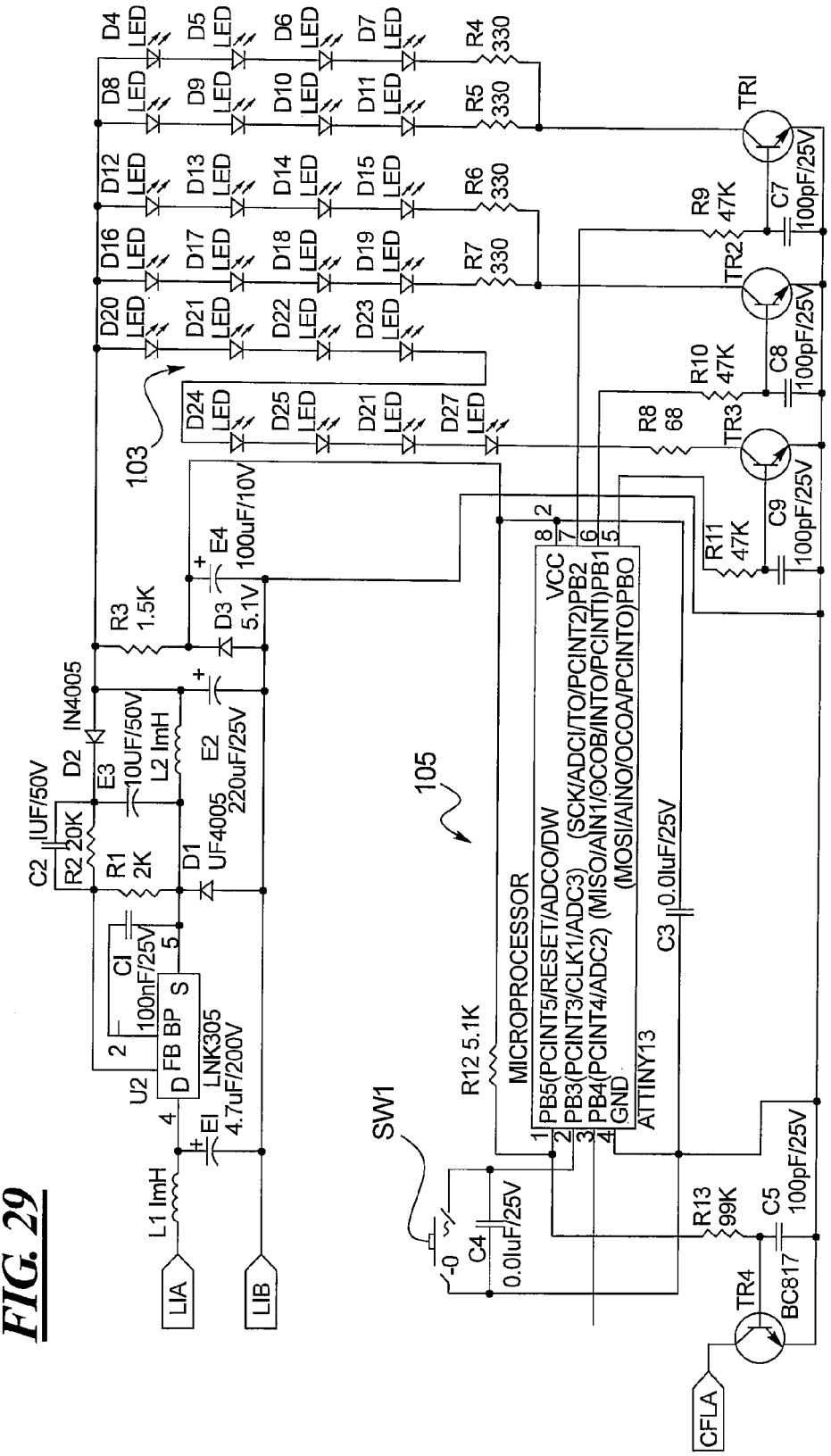
FIG. 29 is a circuit diagram of an exemplary LED driver circuit and corresponding LED array for the accessory shown in FIGS. 26-27, and may linked to the circuitry of FIG. 9.

Turning to FIG. 29, the LED array 103 may include any number of LEDs, although eight RGB clusters are shown in FIG. 29. The device 101 will most likely include 21 LEDs or seven RGB clusters or less. The LEDs 103 are connected in series with the transformer T1 of FIG. 9 as shown by the label CFLA at the lower left in FIG. 29 and at the top of the FIG. 9.

Returning to FIG, 29, the light show circuitry includes the microcontroller U1 having a memory for storing three different light shows. The single switch SW1 is a button that, when first pushed, allows the LED driver 105 to be powered up. The LED driver 105 can be considered everything below and to the left of the LED array 103 which is shown in the upper right-hand corner of FIG. 28. Subsequent pushing of the switch SW1 allows the user to switch between three light shows, power the unit 101 off. The button sequence is listed below:

| | |
|---|---|
| 1 -INITIAL STATE (Power up) | LEDs OFF |
| 2 BUTTON PUSHED | EXECUTE LIGHT SHOW # 1 |
| 3 BUTTON PUSHED | EXECUTE LIGHT SHOW # 2 |
| 4 BUTTON PUSHED | EXECUTE LIGHT SHOW # 3 |
| 5 BUTTON PUSHED | UNIT OFF |

Each group of series-connected LEDs 103 is isolated from the microprocessor U1 by a transistor TR1, TR2 or TR3 for selectively shunting around the group of LEDs 103 and protecting the microprocessor U1 from the higher operating voltage of the LEDs 103. Based on the switch SW1 sequence, the microprocessor U1 sends a control signal to control the transistors TR1-TR3, which in turn control the LED array 103 as described above. When the LED driver 105 is turned on, current flows through the inductor L1 and capacitor E1 to provide a DC voltage across E1. The DC voltage across E1 drives a switching power supply that is operated in constant current power mode, comprising an integrated power metal oxide field effect transistor (MOSFET) in the regulator module U2, the inductor L2, diode D1, and the capacitors E3 and C2.

Regulator module U2 is a high frequency switching buck-boost converter, such as part number LNK 305 as shown Control module U2 has 4 pins: FB=feedback, BP=bypass, D=drain, and S=source. The control module U2, inductor L2, diode D1, and capacitors C2 and E3 are configured in a buck-boost topology, to lower the line voltage to that needed to drive the LEDs A current sense resistor R1 provides a sample of the load current back to the control module U2, to set the current provided by the power supply in constant current mode.

The internal MOSFET of regulator module U2 conducts or is "on" when the BP pin voltage exceeds a predetermined voltage, e.g. 4.85V, and the input current delivered to the FB pin is less than a predetermined amperage, e.g., 49 µA. If a current in excess of the predetermined amperage is applied to the FB pin, the internal MOSFET does not conduct, or remains "off." When the internal MOSFET of regulator module U2 is on, current is delivered to the LEDs 103 via inductor L2 and diodes D3 and D2. When the internal MOSFET of regulator module U2 is off, stored energy in inductor L2 delivers power to the load via diodes D3 and D2.

Microprocessor U1 is programmed such that, when powered, it outputs three pulse width modulation (PWM) signals at pins 5, 6, and 7. The PWM signals are coupled directly to the transistors TR1-3. When pins 5, 6, and/or 7 of the microprocessor U1 provide a logical high (5V) signal to one of the transistors TR1, TR2 or TR3, the transistor opens or is turned off. When pins 5, 6, and/or 7 of the microprocessor U1 provide a logical low (OV) signal to one of the transistors TR1, TR2 or TR3, the transistor closes or is turned on. When the transistors TR1-TR3 are off (open), current flows from the regulator module U2 through the LED load. When the transistors TR1-TR3 are on (closed) current is diverted away from the LEDs 103 and is shunted around the LEDs 103 associated with each closed transistor TR1-TR3. Since there is independent control of each transistor, current can be diverted away from each individual group of LEDs 103. In this way, the microprocessor U1 can use PWM to control the LED current in each group or color of LEDs 103 individually.

The average current applied to each group of LEDs can be adjusted by changing the duty cycle of the PWM signal applied to that group through the opening and closing of the transistors TR1-TR3. Thus, by adjusting the duty cycle applied to each transistor TR1-TR3, the average current applied to each group of LEDs 103 per cycle can be adjusted, and hence the brightness/intensity of each group can be adjusted. The capacitor E4 connected between the output of the switching power supply and the power return helps to stabilize the switching power supply by providing load current smoothing, such that the current supplied to the LEDs 103 is approximately DC with a small amount of AC ripple. Capacitor E4 also provides a modest amount of filtering for the power supply. Additional capacitance is distributed among capacitors C7, C8, and C9, which are arranged in parallel with the transistors TR1-TR3. The distributed capacitance arrangement suppresses the LED pulse currents delivered by capacitor E4 when any of the transistors TR1-TR3 are closed.

The LEDs 103 may also be operated as described in commonly assigned International Publication No. WO2005/003625, U.S. Publication Nos. US 2005/0169812 and US 2005/0169666, all of which are incorporated herein by reference.

Figure 31:
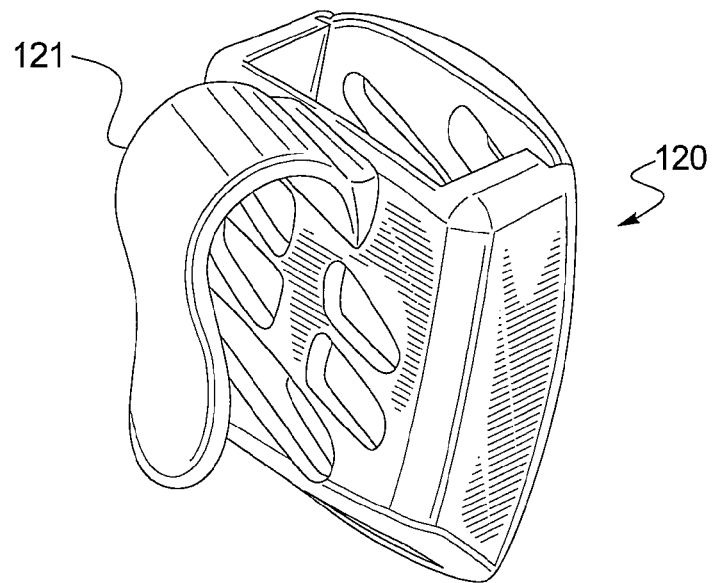
FIG. 31 is a rear perspective view of the volatile active cartridge clip shown in FIG. 30.
Figure 32:
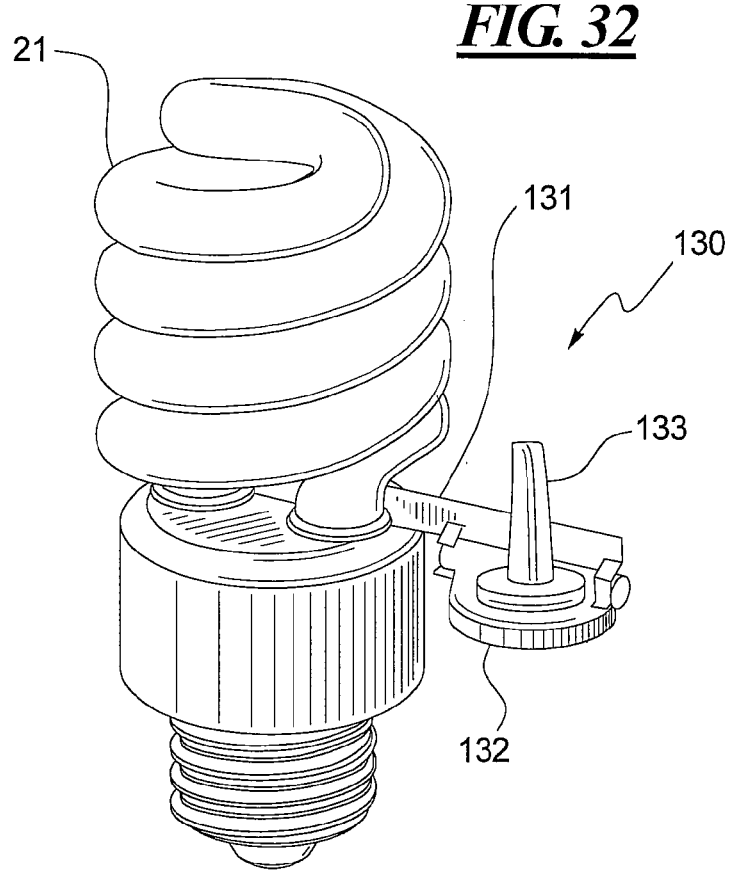
FIG. 32 is a perspective view of another volatile active dispensing device that may be attached to a CFL tube for use in conjunction with other embodiments shown herein.

Turning to FIGS. 30-32, two additional devices for emitting active materials are disclosed. In FIGS. 30-31 a fragrance dispenser 120 is disclosed with a flexible clip 121 that may be used to mount the dispenser 120 on the CFL tube 21. This device 120 is particularly useful when the LED/colored light show accessory 101 is being used. In FIG. 32, a dispenser 130 is disclosed that includes in metallic bracket 131 that clips onto or otherwise engages the CFL tube 21 and conducts heat to the active container 132 which includes a wick 133.

As shown in FIG. 5, a female socket 85 may also be installed on the device 20 which includes a non-removable dispenser 25. Further, as shown in FIG. 22, an additional socket 85 is shown in phantom lines. Accordingly, the disclosed devices may accommodate multiple dispensers for emitting combinations of actives or fragrances or a combination of an LED/colored light show accessory with a volatile active dispenser.

An ingredient suitable for inclusion in the evaporative cartridges, bottles or packages disclosed herein, or passive dispensers disclosed herein, is a fragrance, air freshener, deodorizer, odor eliminator, malodor counteractant, insecticide, insect repellant, medicinal substance, aromatherapy substance, disinfectant, sanitizer, mood enhancer, or the like, in liquid, oil or gel form, although gels and oils are preferred.

Preferably, if a fragrance is to be dispensed, the fragrance or air freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components. Synthetic types of fragrance compositions either alone or in combination with natural oils are described in U.S. Pat. Nos. 4,324,915, 4,411,829; and 4,434,306, which are incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. A fragrance ingredient can also be in the form of a crystalline solid, which has the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability to an air freshener dispenser device for use with the devices disclosed herein.

Suitable insect repellents, insect attractants and insecticides are well-known and will be apparent to those skilled in the art. Regarding the use of insect control actives, the disclosed devices may be particularly useful for patio/deck lighting and outdoor promoter lighting where it is desirable to keep insects away from a defined area such as a patio, deck or pool area and/or where it is desirable to attract insects away from such a defined area. Still further, use of the disclosed devices in an enclosed area such as the closet provides the opportunity for the volatile active to be a moth, cockroach, housefly, fruit fly, ant, gnat or other household insect killer or repellent.

INDUSTRIAL APPLICABILITY

The devices of this disclosure make it possible to combine energy-efficient white light emission with active ingredient emission in a single device that can serve as a substitute for conventional incandescent light bulb.

While only certain embodiments have been set forth, alternatives and modifications will be apparent from the above description to those skilled in the art. These and other alternatives are considered equivalents and within the spirit and scope of this disclosure and the appended claims.

What is claimed:

1. A combination light source and volatile active dispenser device, comprising:
a base connected to a volatile active dispenser, the base supporting a light source, the base being disposed between the light source and a male connector for engaging a light socket,
the volatile active dispenser extending radially outwardly from one side of the base, the volatile active dispenser comprising an decorative outer grill and a slot disposed between the grill and said one side of the base, the slot and decorative outer grill being disposed tangentially to the base, the slot for mateably receiving a replaceable cartridge containing an active material, the replaceable cartridge comprising a porous front panel, the slot and replaceable cartridge being configured to require the porous front panel of the cartridge to face the decorative outer grill when the replaceable cartridge is received in the slot to vent the active material through the porous front panel and radially outward through the decorative outer grill.

2. The device of claim 1 wherein the base houses control circuitry for operating the light source.

3. The device of claim 2 wherein the base houses circuitry for a heater used to heat the replaceable cartridge.

4. The device of claim 1 wherein the light source comprises a low voltage white light source.

5. The device of claim 1 wherein the light source comprises one or mote white light emitting diodes (LEDs).

6. The device of claim 1 wherein the base comprises a sidewall that comprises at least one socket for mounting an accessory to the base, the accessory being selected from the group consisting of a fan, and a colored light device that comprises a plurality of colored LEDs.

7. The device according to claim 1, wherein the active ingredient in the replaceable cartridge is selected from the group consisting of a flagrance, an air sanitizer, an air deodorizer, an insecticide, an insect repellant, an insect attractant, a medicine, an aromatherapy oil, and combinations thereof.

8. The device of claim 1 wherein the male connector comprises first and second semi-cylindrical halves, the first semi-cylindrical half being fixed in position with respect to the base, the second semi-cylindrical half being movable from an outwardly biased position towards the first semi-cylindrical halt, whereby movement of the second semi-cylindrical half towards the first semi-cylindrical half reduces an effective outer diameter of the male connector thereby enabling the male connector to be stabbed into a female receptacle.

9. The device of claim 8, wherein the male connector further comprises a spring-biased pin extending axially between the first and second semi-cylindrical halves for enhancing electrical connection between a male connector and a female receptacle.

10. The device of claim 8 wherein the base further comprises an actuator for moving the second semi-cylindrical half from the outwardly biased position towards the first semi-cylindrical half.

11. The device of claim 1 wherein the male connector is rotatable with respect to the base and light source.

12. The device of claim 11 further comprising an actuator disposed between the base and the male connector for imparting movement to the male connector.

13. The device of claim 12 wherein the actuator is a thumbwheel.

14. The device of claim 1 wherein the base comprises a cylindrical structure disposed between the male connector and the light source, the volatile active dispenser comprising a sleeve with a cylindrical through-opening for receiving the cylindrical structure of the base, the sleeve further comprising slot for receiving the container replaceable cartridge, the sleeve being rotatable with respect to the cylindrical structure of the base, the male connector and the light source.

15. The device of claim 14 wherein the cylindrical structure of the base comprises at least one electrical contact and the cylindrical through-opening of the dispenser comprises at least one electrical contact for engagement with the least one electrical contact of the base, the at least one electrical contact of the dispenser being connected to a heating element for delivering heat to the replaceable cartridge.

16. A combination compact fluorescent light (CFL) and volatile active dispenser device, comprising:

a base connected to a volatile active dispenser, the base supporting the CFL, the base being disposed between the CFL and a male connector for engaging a light socket, the volatile active dispenser extending radially outwardly from one side of the base, the volatile active dispenser comprising a shaped slot for receiving a replaceable cartridge containing an active material, the volatile active dispenser further comprising a decorative outer grill through which active vapor can pass, the shaped slot and decorative outer grill being disposed tangentially to the base, the shaped slot being disclosed between the base and the decorative outer grill, the replaceable cartridge comprising a porous font panel for releasing the active material, the replaceable cartridge having a shaped cross section that requires the porous front panel to face radially outward away from the base and towards the decorative outer grill when the replaceable cartridge is received in the slot, the base comprising a heater disposed opposite the slot from the decorative outer grill.

17. The device of claim 16 wherein the male connector is rotatable independent of the volatile active dispenser.

\* \* \* \* \*

UNITED STATES PATENT AND TRADEMARK OFFICE
CERTIFICATE OF CORRECTION

PATENT NO. : 7,618,151 B2  Page 1 of 1
APPLICATION NO. : 12/057049
DATED : November 17, 2009
INVENTOR(S) : Matthew Abbondanzio et al.

It is certified that error appears in the above-identified patent and that said Letters Patent is hereby corrected as shown below:

In the Claims:

Column 15, Line 31, Claim 14: delete "container"

Column 16, Line 23, Claim 16: replace "font" with --front--

Signed and Sealed this

Ninth Day of November, 2010

David J. Kappos
*Director of the United States Patent and Trademark Office*